United States Patent [19]

Nelson et al.

[11] Patent Number: 5,955,729
[45] Date of Patent: Sep. 21, 1999

[54] SURFACE PLASMON RESONANCE-MASS SPECTROMETRY

[75] Inventors: Randall W. Nelson, Ahwahtukee; Jennifer R. Krone, Phoenix, both of Ariz.; Russell Granzow, Easton, Pa.; Östen Jansson, Storvreta; Stefan Sjölander, Bärby Fundbo, both of Sweden

[73] Assignee: Biacore AB, Sweden

[21] Appl. No.: 08/708,341

[22] Filed: Sep. 6, 1996

[30]      Foreign Application Priority Data

Sep. 8, 1995 [GB] United Kingdom ............ 9518429

[51] Int. Cl.$^6$ ............... B01D 59/44; H01J 49/00
[52] U.S. Cl. .............. 250/282; 250/288; 250/423 P
[58] Field of Search ................. 250/282, 288, 250/292, 423 P

[56]           References Cited

U.S. PATENT DOCUMENTS

| | | | |
|---|---|---|---|
| 3,896,661 | 7/1975 | Parkhurst et al. | 73/61.1 |
| 4,214,159 | 7/1980 | Hillenkamp et al. | 250/423 P |
| 4,686,366 | 8/1987 | Stuke | 250/423 P |
| 5,017,007 | 5/1991 | Milne et al. | 356/301 |
| 5,045,694 | 9/1991 | Beavis et al. | 250/423 P |
| 5,118,937 | 6/1992 | Hillenkamp et al. | 250/423 P |
| 5,359,681 | 10/1994 | Jorgenson et al. | 385/12 |
| 5,376,336 | 12/1994 | Lubbers et al. | 422/82.06 |
| 5,395,587 | 3/1995 | Brigham-Burke et al. | 422/68.1 |
| 5,647,030 | 7/1997 | Jorgenson et al. | 385/12 |
| 5,705,813 | 1/1998 | Apffel et al. | 250/288 |
| 5,719,060 | 2/1998 | Hutchens et al. | 436/174 |

FOREIGN PATENT DOCUMENTS

| | | |
|---|---|---|
| 464 120 B1 | 1/1992 | European Pat. Off. . |
| 2236185 | 3/1991 | United Kingdom . |
| WO 90/05295 | 5/1990 | WIPO . |
| WO 90/05303 | 5/1990 | WIPO . |
| WO 90/05305 | 5/1990 | WIPO . |
| WO 93/25910 | 12/1993 | WIPO . |
| WO 94/28418 | 12/1994 | WIPO . |

OTHER PUBLICATIONS

BIA Journal, "Analysis at the speed of light," *BIAjournal* 1:4–5, 1994.

Dogruel et al. "Rapid Protein Characterization Using Bioreactive Mass Spectrometer Probe Tips," *Presented at the Association of Bimolecular Resource Facilities (ABRF) Meeting* Held Mar. 30–Apr. 2, 1996.

Dogruel et al., "Rapid Tyrptic Mapping Using Enzymatically Active Mass Spectrometer Probe Tips," *Anal. Chem.* 67(23): 4343–4348, 1995.

Hutchens & Yip, "New Desorption Strategies for the Mass Spectrometric Analysis of Macromolecules," *Rapid Commun. Mass Spectrom.* 7:576–580, 1993.

Jansson and Sönksen, "BIA—MS: Molecular weight determination of protein eluted from a sensor chip," *Biosensor*, 1996.

(List continued on next page.)

*Primary Examiner*—Bruce Anderson
*Attorney, Agent, or Firm*—Seed and Berry LLP

[57]           ABSTRACT

The invention provides surface plasmon resonance-mass spectroscopy for the rapid, sensitive and accurate investigation of molecular interactions coupled with the identification and quantification of the same. Methods of the invention include capturing an analyte present within a sample by an interactive surface layer on a real-time interaction analysis sensor, analyzing the analyte by surface plasmon resonance while the analyte is captured by the interactive surface layer, and identifying the captured analyte by desorbing/ionizing the analyte from the interactive surface layer while under vacuum within a mass spectrometer. Devices of the invention include a transparent material, a conductive material capable of supporting surface plasmon resonance affixed to the transparent material, an interactive surface affixed to the conductive material, and a means for exposing the interactive surface to the interior of a mass spectrometer without breaking the vacuum therein.

17 Claims, 21 Drawing Sheets

OTHER PUBLICATIONS

Johnsson et al., "Immobilization of Proteins to a Carboxymethyldextran–Modified Gold Surface for Biospecific Interaction Analysis in Surface Plasmon Resonance Sensors," *Anal. Biochem.* 198:268–277, 1991.

Jönsson et al., "Real–Time Biospecific Interaction Analysis Using Surface Plasmon Resonance and a Sensor Chip Technology," *Bio Techniques* 11(5):620–627, 1991.

Krone, et al., "Interfacing Mass Spectrometric Immunoassays with BIA," *BIAjournal* 3(1):16–17, 1996.

Löfås and Johnsson, "A Novel Hydrogel Matrix on Gold Surfaces in Surface Plasmon Resonance Sensors for Fast and Efficient Covalent Immobilization of Ligands," *J. Chem. Soc., Chem.. Comm.21*: 1526–1528, 1990.

Malmqvist, M., "Surface Plasmon Resonance for Detection and Measurement of Antibody–Antigen Affinity and Kinetics," *Current Opinion in Immunology* 5:282–286, 1993.

Nelson et al., "Mass Spectrometric Immunoassay," *Anal. Chem.* 67(7):1153–1158, 1995.

Nelson et al., "Mass Spectrometric Immunoassay and Interfacing BIA with MS," 1995.

Nelson et al., "Peptide Characterization Using Bioreactive Mass Spectrometer Probe Tips," *Rapid Comm. Mass Spectrometry* 9:1380–1385, 1995.

Save et al., "Spin–Deposited Submicrometer Films of Organic Molecules for Secondary Ion Mass Spectrometry Studies," *Anal. Chem.* 59:2059–2063, 1987.

Voivodov et al., "Surface Arrays of Energy Absorbing Polymers Enabling Covalent Attachment of Biomolecules for Subsequent Laser–Induced Uncoupling/Desorption," *Tet. Letters* 37(32):5669–5672, 1996.

International Preliminary Examination Report, For PCT Patent Application PCT/US96/14372, Dec. 22, 1997.

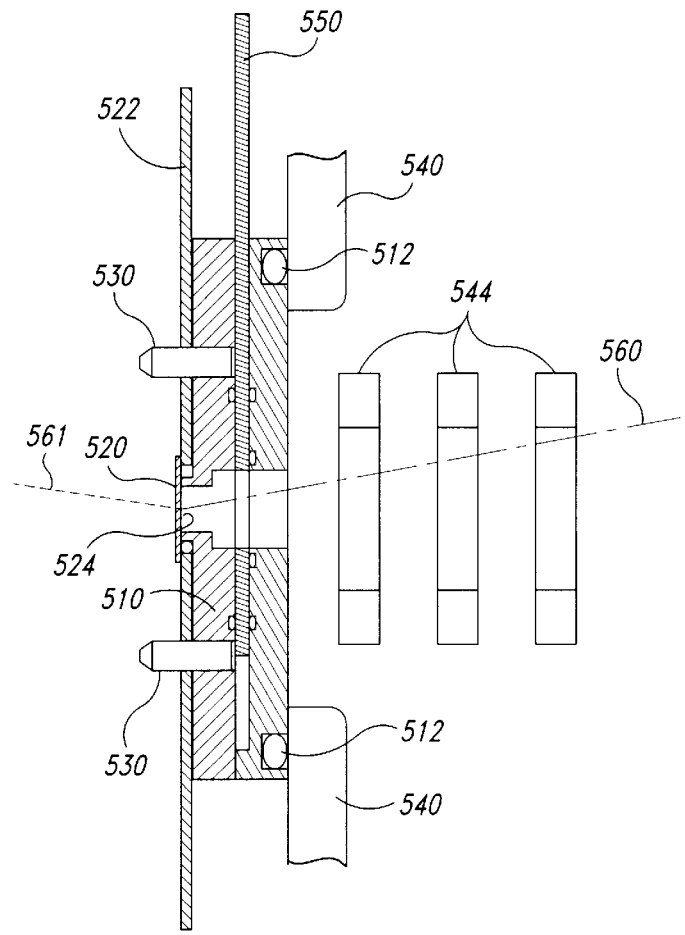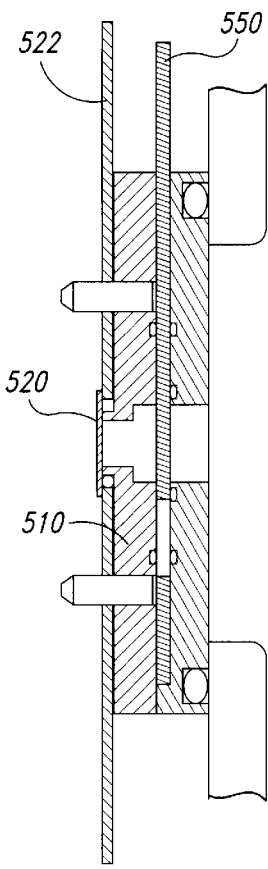
Fig. 5A
Fig. 5B
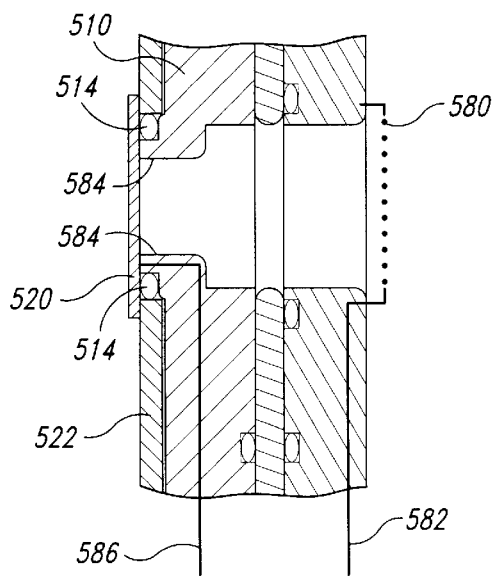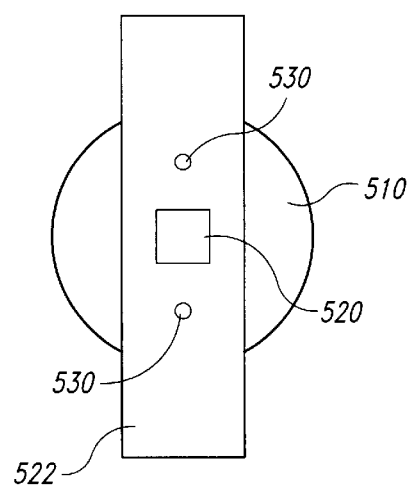
Fig. 5C
Fig. 5D

Fig. 9

SURFACE PLASMON RESONANCE-MASS SPECTROMETRY

CROSS-REFERENCE TO RELATED APPLICATION

This application claims priority from UK Provisional Application No. GB 9518429.7, filed Sep. 8, 1995.

TECHNICAL FIELD

This invention is generally directed to surface plasmon resonance-mass spectrometry (SPR-MS) and, more specifically, to apparatuses and methods for the rapid, sensitive and accurate investigation of molecular interactions coupled with the identification and quantification of the same.

BACKGROUND OF THE INVENTION

In 1987, matrix-assisted laser desorption/ionization mass spectrometry (MALDI) was introduced by Hillenkamp and Karas, and since has become a very powerful bioanalytical tool (*Anal. Chem.* 60:2288–2301, 1988; see also Burlingame et al., *Anal. Chem.* 68:599–651, 1996 and references cited therein). The success of MALDI in the area of protein science can be attributed to several factors. The greatest of these is that MALDI can be rapidly (~5 minutes) applied as an analytical technique to analyze small quantities of virtually any protein (practical sensitivities of ~1 pmole protein loaded into the mass spectrometer). The technique is also extremely accurate. Beavis and Chait demonstrated that the molecular weights of peptides and proteins can be determined to within ~0.01% by using methods in which internal mass calibrants (x-axis calibration) are introduced into the analysis (*Anal Chem.* 62:1836–40, 1990). MALDI can also be made quantitative using a similar method in which internal reference standards are introduced into the analysis for ion signal normalization (y-axis calibration). Quantitative determination of proteins and peptides is possible using this approach with accuracy's on the order of ~10% (Nelson et al., *Anal. Chem.* 66:1408–15, 1994). Finally, MALDI is extremely tolerant of large molar excesses of buffer salts and, more importantly, the presence of other proteins.

With the high tolerance towards buffer salts and other biomolecular components comes the ability to directly analyze complex biological mixtures. Many examples exist where LDI is used to directly analyze the results of proteolytic or chemical digestion of polypeptides (see Burlingame et al., supra). Other examples extend to elucidating post-translational modifications (namely carbohydrate type and content), a process requiring the simultaneous analysis of components present in a heterogeneous glycoprotein mixture (Sutton et al., *Techniques in Protein Chemisty III*, Angeletti, Ed., Academic Press, Inc., New York, pp. 109–116, 1993). Arguably, the most impressive use of direct mixture analysis is the screening of natural biological fluids. In that application, proteins are identified, as prepared directly from the host fluid, by detection at precise and characteristic mass-to-charge (m/z) values (Tempst et al., *Mass Spectrometry in the Biological Sciences*, Burlingame and Carr, Ed., Humana Press, Totowa, N.J., p. 105, 1996).

While the above examples involving direct MALDI analysis of complex mixtures are, in their own right, quite impressive, there exist limits to the extent of practical application. These limits are reached when a target analyte is a minor component of the mixture, and is present at low concentration. A common occurrence in such situations is that the target analyte is never observed in the MALDI mass spectrum. This lack of detection is generally due to the low concentration of the analyte yielding ion signals at or below the instrumental limits of detection—an effect further exacerbated by protein-analyte interactions "stealing" analyte molecules from the MALDI process, and/or high instrumental baselines produced from other proteins present in the mixture ("analyte masking"). Methods for the selective concentration of specific species in the mixture (prior to MALDI) are therefore required in order to achieve ion signals from the target analyte.

The use of an affinity ligand-derivatized support to selectively retrieve a target analyte specifically for MALDI analysis was first demonstrated by Hutchens and Yip (*Rapid Commun. Mass Spectrom.* 7:576–80, 1993). Those investigators used single-stranded DNA-derivatized agarose beads to selectively retrieve a protein, lactoferrin, from pre-term infant urine by incubating the beads with urine. The agarose beads were then treated as the MALDI analyte—a process involving mixing with a solution-phase MALDI matrix followed by deposition of the mixture on a mass spectrometer probe. MALDI then proceeded in the usual manner. Results indicated that the derivatized beads selectively retrieved and concentrated the lactoferrin; enough so to enable ion signal in the MALDI mass spectrum adequate to unambiguously identify the analyte at the appropriate m/z value (81,000 Da). A number of variations on this approach have since been reported. These include the use of immunoaffinity precipitation for the MALDI analysis of transferring in serum Nakanishi et al., *Biol. Mass Spectrom.* 23:230–33, 1994), screening of ascites for the production of monoclonal antibodies (Papac et al., *Anal. Chem.* 66:2609–13, 1994), and the identification of linear epitope regions within an antigen (Zhao et al., *Anal. Chem.* 66:3723–26, 1994). Even more recently, the affinity capture approaches have been made rigorously quantitative by incorporating mass-shifted variants of the analyte into the analysis (Nelson et al. *Anal. Chem.* 67:1153–58, 1995). The variants are retained throughout the analysis (in the same manner as the true analyte) and observed as unique (resolved) signals in the MALDI mass spectrum. Quantitation of the analyte is performed by equating the relative ion signals of the analyte and variant to an analyte concentration.

The affinity capture techniques discussed above make use of "off-line" incubation steps. That is, the target analyte is captured on some form of affinity-derivatized support (generally chromatographic beads) and then eluted onto a mass spectrometer probe tip. Use of such off-line approaches have generally been considered advantageous because relatively large quantities of affinity-derivatized reagent (and hence large quantities of affinity ligand) can be used in a given analysis. These techniques can also be performed in a flowing manner, with large volumes of analyte solution and wash buffers brought in contact with the affinity reagent. As a result, the affinity capture steps are fast (~5 min) and clean (low non-specific binding).

An attractive alternative to using beaded material in an off-line approach is to incorporate the affinity ligand directly onto the mass spectrometer probe element. This would allow the probe to be used to selectively retrieve and retain an analyte from solution, and then be MALDI-analyzed (bypassing any elution steps). Although there have been some attempts to use a LDI mass spectrometer probe element as the affinity-capture device (Brockman et al., *Anal. Chem.* 67:4581–85, 1995), such attempts have fallen short of expectation. This downfall is due mainly to the severe limitation on the number of surface-active affinity sites possible on the essentially two-dimensional surface of the mass spectrometer probe. As a result, such derivatized-probes are neither as sensitive or as rapid as the off-line approaches. A second, more fundamental issue deals with analyte utilization. In the aforementioned analyses, affinity interactions are used solely to define the species introduced into the mass spectrometer—mass spectrometry, as a destructive technique, then destroys the analyte.

Accordingly, there still exists a need in the art for improved analytical techniques, particularly in the field of mass spectrometry. Such techniques should be capable of analyzing complex mixtures while overcoming the disadvantages associated with existing off-line incubation steps, as well as provide information in addition to mere species identification. The present invention fulfills these needs, and provides further related advantages.

SUMMARY OF THE INVENTION

Briefly stated, this invention is directed to surface plasmon resonance-mass spectroscopy (hereinafter referred to as "SPR-MS") and, more specifically, to various methods and apparatuses relating to SPR-MS. Within the context of this invention, SPR-MS provides real-time information regarding molecular interactions, as well as capturing an analyte from a sample, thus localizing and concentrating the analyte for identification and/or quantification by mass spectroscopy.

In one embodiment, a method for performing surface plasmon resonance-mass spectroscopy on a sample is disclosed. The method involves capturing an analyte present within the sample by an interactive surface layer of an interaction analysis (IA) sensor; analyzing the analyte by surface plasmon resonance while the analyte is captured by the interactive surface layer of the IA sensor; and identifying the captured analyte by desorbing/ionizing the analyte from the interactive surface layer of the IA sensor while under vacuum within a mass spectrometer. Suitable IA sensors include both chip- and fiber optic-based sensors.

In another embodiment, there is disclosed a method for analyzing and identifying an analyte within a sample. The method involves capturing the analyte by contacting the analyte with an interactive surface layer affixed to a conductive material capable of supporting surface plasmon resonance, wherein the conductive material has a front surface affixed to the interactive surface layer and a back surface affixed to a transparent layer; directing light through the transparent layer at varying angles of incidence or wavelength such that the light is reflected off the back surface of the conductive material and excites surface plasmons at the interface between the conductive layer and the interactive surface layer; detecting the angle of incidence or the wavelength at which the intensity of the reflected light has a minimum due to surface plasmon resonance to determine the angular or wavelength change caused by the analyte captured by the interactive surface layer; and measuring the mass spectrum of the analyte by desorbing/ionizing the analyte from the interactive surface layer while under vacuum within a mass spectrometer. In this embodiment, the interactive surface layer affixed to the conductive material and the transparent layer may be in the form of a chip or fiber optic.

Suitable interactive surface layers include hydrogels generally and, more specifically, a hydrogel of a polysaccharide such as carboxymethylated dextran. Suitable conductive materials include metals, such as gold and silver, and the transparent layer may be a glass. The analyte may be desorbed/ionized by a laser striking the interactive surface layer by, for example directing the laser light such that it passes through the interactive layer before striking the front surface of the conductive material, or such that it strikes the back surface of the conductive material and passes through the conductive material and into the interactive layer. A suitable laser desorption/ionization matrix may also be employed.

In yet a further embodiment, a surface plasmon resonance-mass spectroscopy (SPR-MS) device is disclosed. Such a SPR-MS device comprises a transparent material; a conductive material capable of supporting surface plasmon resonance affixed to the transparent material; an interactive surface affixed to the conductive material; and means for exposing the interactive surface to the interior of a mass spectrometer without breaking the vacuum therein. In one aspect of this embodiment, the conductive material may be in electrical contact with the mass spectrometer.

Suitable exposing means include a metal probe, wherein the transparent material is affixed thereto, and wherein the conductive material may optionally be in electrical contact with the metal probe. Alternatively, the SPR-MS device may be a non-conducting material, and the conductive material may be in sealable contact therewith to maintain vacuum within the interior of a mass spectrometer. In this embodiment, suitable transparent materials include glass, and conductive materials include metals such as gold and silver. The interactive surface includes hydrogels, which may optionally be affixed to the conductive material through an appropriate linker.

In a further aspect of this embodiment, the transparent material and conductive material are in the form of a chip or a fiber optic, and the combination of such a chip or fiber optic with a mass spectrometer is disclosed.

These and other aspects of the invention will become apparent upon reference to the following detailed description and attached drawing. To this end, various references are cited throughout the background section and detailed description, each of which is incorporated in its entirety herein by reference.

BRIEF DESCRIPTION OF THE DRAWINGS

FIG. 5A–D illustrates a representative device for associating the interactive layer of an IA sensor chip with the interior of a mass spectrometer.

FIG. 7A is a sensorgram illustrating the immobilization of antimyotoxin a within one flow cell of a BIAcore® (Pharmacia Biosensor AB, Uppsala, Sweden) CM5 chip (approximately 20,000 RU of anti-myotoxin a is immobilized on the derivatized chip and corresponds to a binding capacity of ~300 fmole myotoxin a.

FIG. 9 illustrates the ability of SPR-MS to individually target flow cells of a BIAcore CM5 chip derivatized with anti-myotoxin a (with the exception of flow cell 4 which serves as a blank) and then incubated with the C.v. viridis rattlesnake venom. Specifically, the mass spectra obtained from the interactive surface of each of the four flow cells is presented, with myotoxin a observed in all but flow cell 4. Marker proteins, angiotensin II (flow cells 1 and 3) and secretin (flow cells 2 and 4), were added in with a MALDI matrix to demonstrate spatial resolution and also serve as internal references (i.e., x-axis, y-axis calibration).

DETAILED DESCRIPTION OF THE INVENTION

As mentioned above, this invention is directed to SPR-MS, as well as to various methods and apparatuses relating thereto. SPR-MS provides real-time information regarding molecular interactions, as well as capturing an analyte from a sample, thus localizing and concentrating the analyte for identification and/or quantification by mass spectroscopy.

In the practice of this invention, SPR-MS employs molecular interaction analysis (IA), such as the technique developed by Pharmacia Biosensor AB (Uppsala, Sweden). IA is a biosensor technology for monitoring interactions, in real time and without the use of labels, between two or more molecules such as proteins, peptides, nucleic acids, carbohydrates, lipids and low molecular weight molecules, such as signaling substances and pharmaceuticals. Molecules do not need to be purified or even solubilized, but can be studied in crude extracts as well as anchored in lipid vesicles, viruses, bacteria and eucaryotic cells.

The detection principle relies on the optical phenomenon of surface plasmon resonance (SPR), which detects changes in the refractive index of the solution close to the surface of a sensor chip. This is in turn directly related to the concentration of solute in the surface layer. In one embodiment, an IA analysis is performed by immobilizing one interactant on the surface of an IA sensor, which, in one embodiment, forms one wall of a micro-flow cell. Sample containing the other interactant(s) is then injected over the surface in a controlled flow. Any change in surface concentration resulting from interaction is detected as an SPR signal, expressed in resonance units (RU).

Figure 1A:
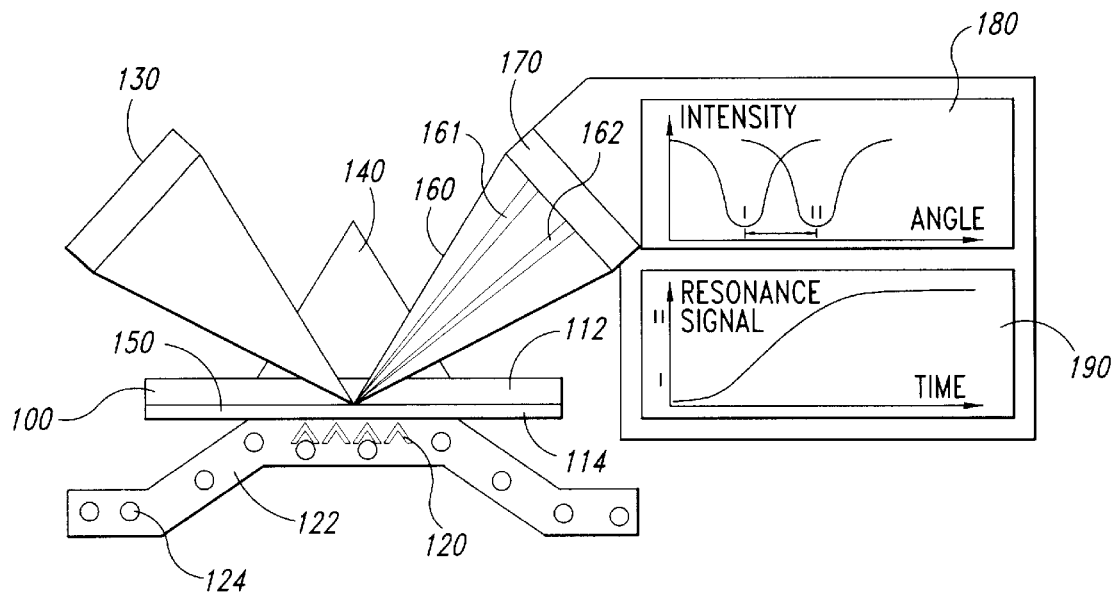
FIG. 1A is a schematic of a prior art device for performing Interaction Analysis (IA) utilizing a chip-based sensor for measuring Surface Plasmon Resonance (SPR) in conjunction with a flow device for sample delivery.

The use of a representative IA sensor chip to perform such an analysis is depicted in FIG. 1A. In this embodiment, sensor chip (100) is a transparent material (112) having a metal layer (114) deposited thereon. Interactants (120), which in FIG. 1A are depicted as antibodies, are immobilized on metal layer (114). Light source (130) generates polarized light which is directed through prism (140), striking the metal layer-transparent material interface (150). (Alternatively, a metalized diffraction grating may be employed.) Reflected light (160) is detected by detector (170). As a sample containing interactact(s) (124) passes through flow channel (122) antibodies (120) selectively bind thereto. This change in surface concentration is detected as an SPR signal by the shifting of reflected intensity signal I (161) to signal II (162) as depicted in graph (180), which plots the change in intensity of the reflected light versus angle of incidence.

Figure 1B:
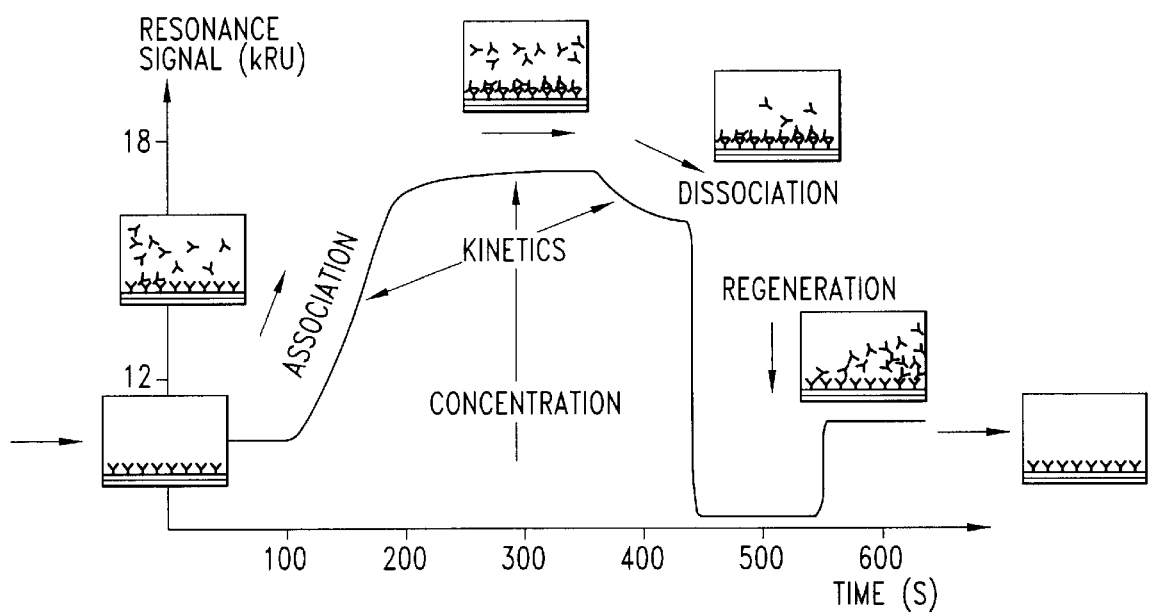
FIG. 1B is a representative sensorgram illustrating association, dissociation and regeneration of the IA sensor chip of FIG. 1A.

The continuous display of RU as a function of time, depicted by graph (190) in FIG. 1A, is referred to as a "sensorgram," and provides a complete record of the progress of association and dissociation. When analysis of one interaction cycle is complete, the surface can be regenerated by treatment with conditions that remove all bound analyte without affecting the activity of the immobilized ligand. A surface with, for example, immobilized antibody can typically be used for more than 50 analysis cycles. This is illustrated by the more detailed sensorgram of FIG. 1B, which depicts an antibody surface interacting with analyte in a sample. During sample injection, an increase in signal is observed due to binding of the analyte (i.e., association) to a steady state condition where the resonance signal plateaus. At the end of sample injection, the sample is replaced with a continuous flow of buffer and decrease in signal reflects the dissociation of analyte from the surface. The surface may then be regenerated for subsequent analysis. The slope of the association/dissociation provide information regarding the kinetics, and the height of the resonance signal represents surface concentration (i.e., the response resulting from an interaction is related to the change in mass concentration on the surface). The specific response is practically the same for all proteins and peptides and is similar for glycoproteins, lipids and nucleic acids. An IA analysis is thus derived entirely from the interaction properties of the ligand on the surface and the analyte in solution.

A variety of techniques may be employed to fix the interactant to the surface of an IA sensor. In general, one of the interacting partners is either directly immobilized to the surface or captured by an immobilized capturing molecule, such as and antibody or receptor. Furthermore, a surface matrix such as a hydrogel of a polysaccharide (e.g., carboxymethylated dextran) may be affixed to the metal layer by a suitable linking layer. Such a surface matrix provides a hydrophilic environment for surface interaction, is amenable to a wide range of generally applicable immobilization chemistries, and can readily immobilize capturing molecules. Additional examples of suitable surface matrixes and related capturing molecules are set forth in PCT International Publication No. Wo 90/05303.

Figure 2A:
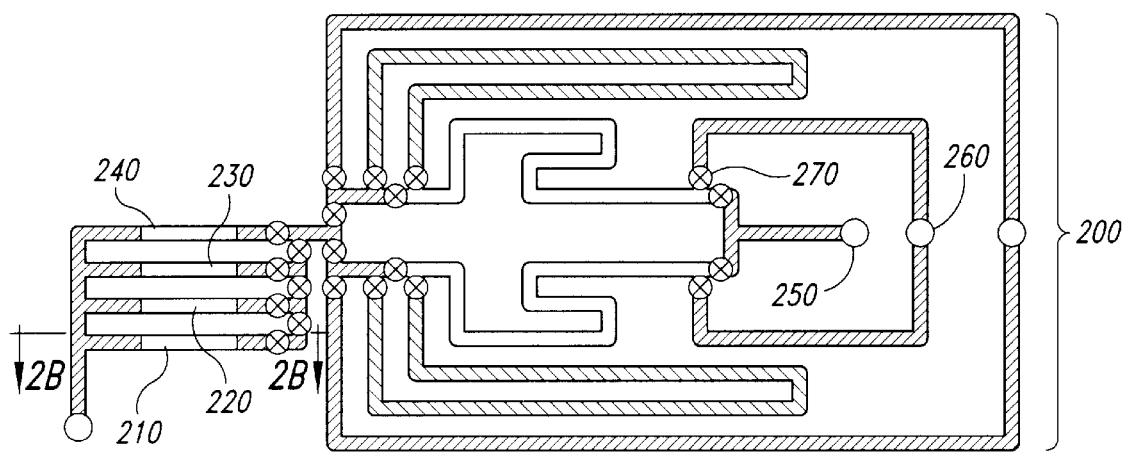
FIG. 2A is a representative prior art flow device for delivery of sample to surfaces of an IA sensor chip having four individual flow cells.
Figure 2B:
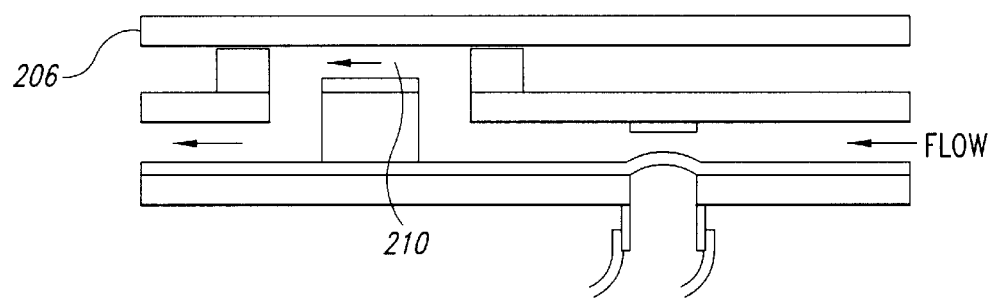
FIG. 2B is a cross-sectional view of a flow cell of FIG. 2A.

A particular advantage of the IA sensor chip is that it can possess a plurality of interactive surfaces in contact with individual flow cells, thus allowing multi-channel analysis of a sample. Such multi-channel IA sensor chips (such as the BIAcore® chip sold by Pharmacia Biosensor AB, Uppsala, Sweden) typically employ a rather sophisticated miniaturized integrated micro-fluidics cartridge as illustrated in FIG. 2A. Samples and reagents are delivered to the chip surface in regulated low volumes by a fully automated delivery flow system. Referring to FIG. 2A, flow system (200) is illustrated having four separate flow channels (210), (220), (230) and (240), respectively, which deliver sample and reagents to the surface of an IA sensor chip (not shown). Sample is introduced through port (250), buffer via port (260), and various valves (270) control delivery of the same to the individual flow channels. A cross-sectional view of flow channel (210) having sensor chip (206) in contact therewith is illustrated in FIG. 2B. While FIG. 2A illustrates a four-channel system, it should be understood that IA sensor chips having a single or any other number of interactive surfaces may be employed.

The IA sensor chips discussed above, as well as instrumentation related to the use thereof, are more filly disclosed in, for example, PCT International Publication Nos. WO 90/05305, WO 90/05295, WO 90/05303, Jönsson et al., BioTechniques 11:620–27, 1991, and Löfås and Jöhnsson, J. Chem. Soc., Chem. Commun., 1526–28, 1990.

While the above disclosure is directed to the use of an IA sensor chip, other IA sensors may also be employed, including, for example, the fiber-optic based IA sensor of PCT International Publication No. WO 94/16312. In this embodiment, the transparent material of the sensor is the optical fiber core. All or a portion of the cladding and/or buffer layer is removed, and a metal layer is deposited on the surface of the bare core to an appropriate thickness to support SPR. A suitable interactant is affixed to the surface of the metal layer such that one of the interacting partners is either directly immobilized to the surface or captured by an immobilized capturing molecule, such as and antibody or receptor. Furthermore, a surface matrix, such as a hydrogel of carboxymethylated dextran, may be affixed to the metal layer by a suitable linking layer to immobilize the capturing molecule. The fiber optic IA sensor is then contacted with the sample and SPR-MS performed as disclosed above. Again, as with the IA sensor chip, single or multi-channel analysis may be performed by employing one or a plurality of fiber optic IA sensors, or by having multiple interactive surfaces on a single fiber optic IA sensor.

In the practice of this invention, the IA sensor is employed to perform real-time analysis. Although IA provides pertinent information on ligand binding and kinetics, identity of the ligand(s) is dependent on the specificity of the affinant and may not always be certain. This is particularly true in complex systems where there exists the potential to bind multiple or unknown ligands, either nonspecifically or in competition for the surface bound affinant. Such nondefined binding is of significant concern. By mass spectrometrically analyzing retained ligands it is possible to detect the presence of nontargeted ligands (with high sensitivity), and to correct for them using quantitative techniques.

To avoid transfer losses and achieve the best sensitivity, ligands are sampled directly from the IA sensor surface rather than eluted into a mass spectrometer. Mass spectrometric methods such as on-chip mapping and sequencing could also be used in conjunction with database searches in the identification of unknown ligands captured from complex samples. The combination of IA and MALDI mass spectrometry allows for rapid, sensitive and accurate investigations of molecular interactions as well as permit new and novel bioanalytical approaches, such as ligand fishing/identification and quantitation, monitoring site-specific kinetics and binding constants, and multiplex diagnostic assays.

In short, the IA sensor is employed as the sample stage for mass spectroscopy. The location of the ion signal on the mass spectrum is dependent upon the molecular weight of the analyte (i.e., the mass-to-charge ratio), thereby identifying the analyte. The mass spectral signal also has magnitude (i.e., height of the signal or area under the same). The magnitude of the signal is indicative of the amount of analyte that is ionized and detected by the mass spectrometer. Suitable mass spectrometers include, but are not limited to, a magnetic sector mass spectrometer, a Fourier transform ion cyclotron resonance (FTICR) mass spectrometer, a quadrapole (rods or ion trap) mass spectrometer and a time-of-flight (TOF) mass spectrometer. In a preferred embodiment, the mass spectrometer is a time TOF mass spectrometer.

Depending upon the size and nature of the analyte captured by the IA sensor, a desorption/ionization matrix material may optionally be employed. Since large molecules, such as peptides and proteins, are generally too large to be desorbed/ionized intact, a matrix is used to assist laser desorption/ionization of the same. This technique is referred to as matrix assisted laser desorption/ionization or (MALDI), and the matrix agent is referred to as a "MALDI matrix." In short, the captured analyte on the IA sensor is contacted with a suitable MALDI matrix and allowed to crystallize on the IA sensor by, for example, drying. Suitable MALDI matrix materials are known to those skilled in this field, and include, for example, derivatives of cinnamic acid such as $\alpha$-cyano-4-hydroxycinnamic acid (ACCA) and sinapinic acid (SA).

Figure 3:
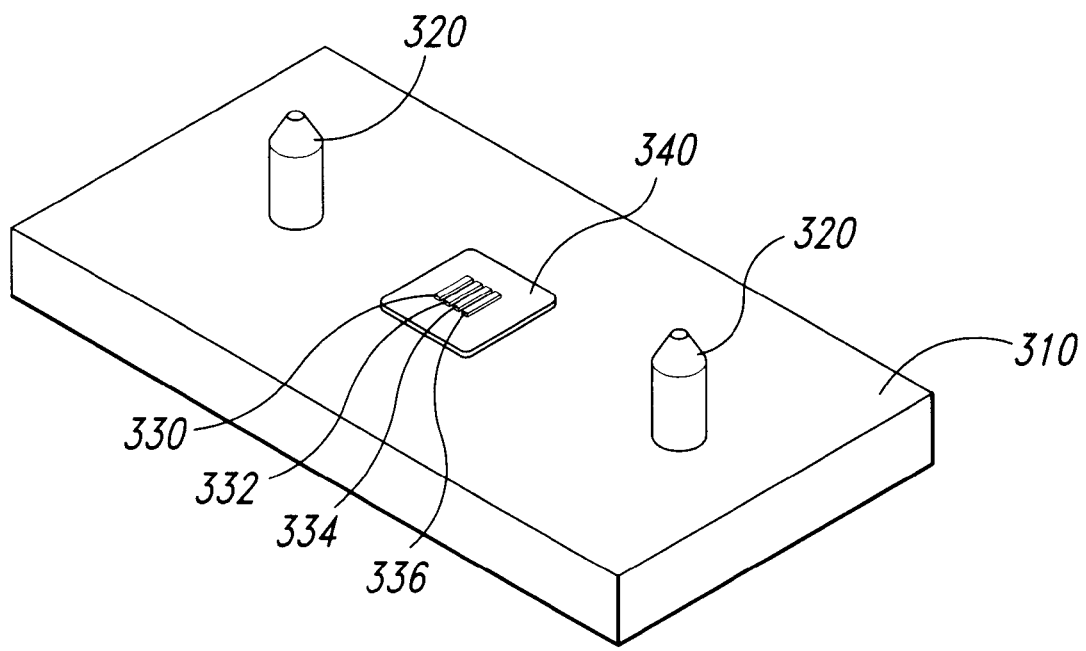
FIG. 3 illustrates a representative applicator for applying a MALDI matrix to the individual interactive layers of an IA sensor chip.

In the case of IA sensor chips, a suitable matrix applicator is illustrated in FIG. 3. Matrix applicator (310) with guide pins (320) affixed thereto, is configured to accept the sensor chip affixed within a suitable chip holder (this aspect of the present invention is more fully discussed below in reference to FIG. 5). An appropriate MALDI matrix is applied to surfaces (330), (332), (334) and (336) of chip receptor (340), and the sensor chip holder (not shown) is positioned such that the individual interactive surfaces of the sensor chip (not shown) is brought in contact with surfaces (330), (332), (334) and (336). In this manner, the same or different MALDI matrix (or matrices) may be applied to the individual interactive surfaces of the IA sensor chip. Alternatively, an ink-jet applicator may be employed, wherein the reservoir or "ink" of the applicator is the MALDI matrix. In this manner, the individual interactive layers of an IA sensor may be individually contacted with the MALDI matrix.

By employing the non-destructive monitoring techniques provided by IA with SPR detection, the affinity interaction is left with the binding partners intact and recoverable for further analysis. Thus, the present invention avoids the destruction of sample via mass spectrometry without first taking advantage of non-destructive affinity interaction assay techniques, thus taking full advantage of both IA and mass spectrometry techniques. Furthermore, real-time non-destructive monitoring can be used to evaluate the initial derivatization of the IA sensor surface (the process of covalently binding the affinant) to ensure the viability of the affinity reagent by determining the quantity of affinant bound to the surface.

Accordingly, in one embodiment a mass spectrometer probe element is disclosed which is capable of providing confirmation that the affinity reagent is properly functioning, prior to mass spectrometry. Moreover, surface reactions beyond covalent coupling and biospecific retention can also be monitored. For example, covalent derivatization of mass spectrometer probe elements with enzymes and/or chemicals may also be employed; the probe device then serving to modify analytes (upon application) for purpose of mass spectrometric characterization. IA sensor surfaces can also be modified and used in the same manner. Surface derivatization and analyte application steps can be monitored in real-time, using non-destructive IA methods, for the verification of reagent and the tracking of the progress of reaction, respectively. The IA sensor surface is then mass spectrometrically analyzed to read the results of the reactions.

Figure 4:
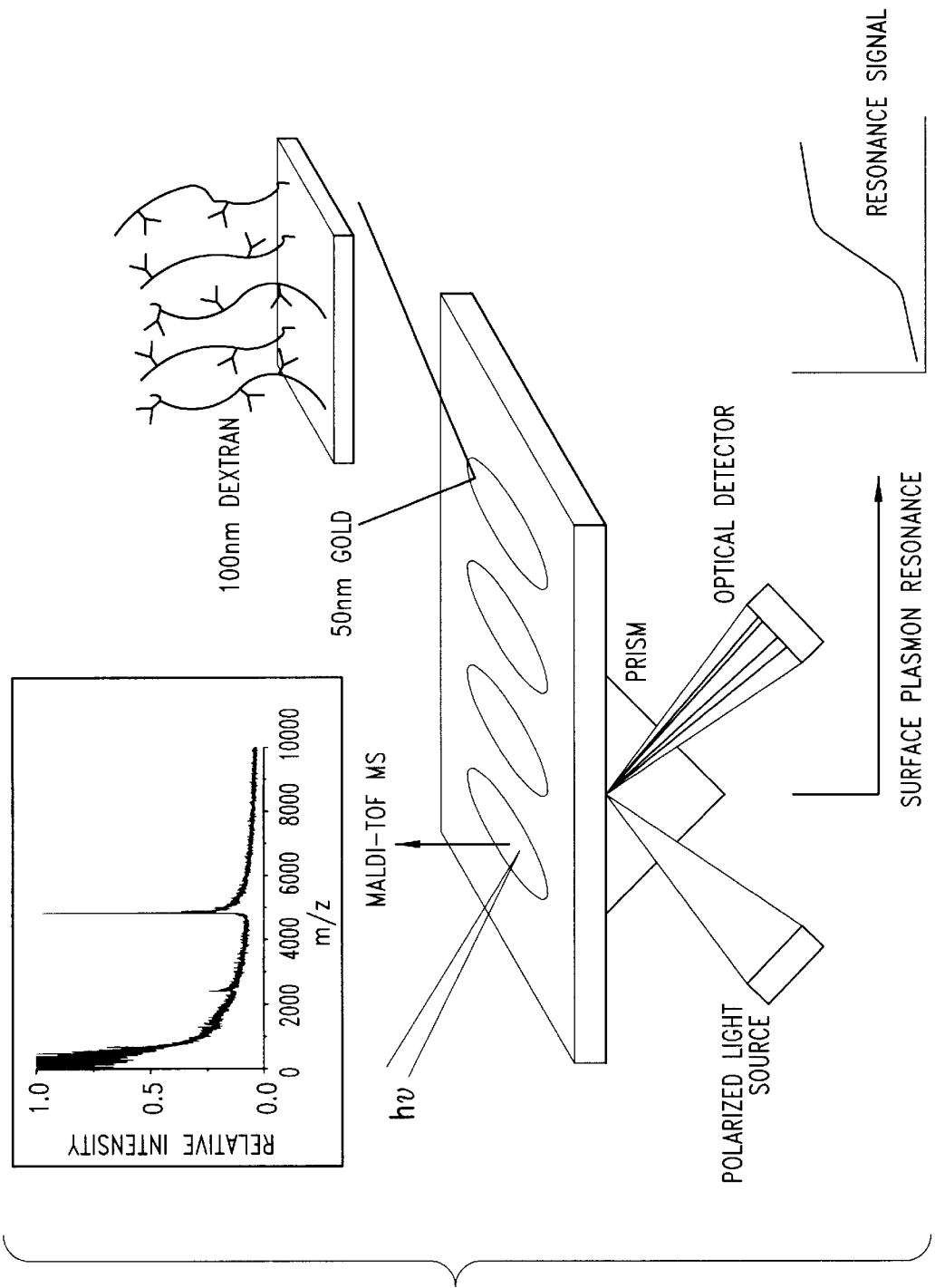
FIG. 4 illustrates SPR-MS according to one embodiment of this invention. A derivatized IA sensor chip (having four interactive surfaces) is used in the real-time SPR analysis of interactions between surface-bound affinant(s) and solution-phase ligand(s), with mass spectrometry following with the retained ligand(s) detected at precise and characteristic m/z values.

FIG. 4 illustrates a representative SPR-MS analysis of this invention. An IA sensor chip having four interactive surfaces, are activated, derivatized with affinant and blocked while continuously monitored using SPR. The derivatized surfaces are then used in real-time IA analysis of interactions between a surface-bound affinant and a solution-phase ligand. The real-time analysis results in biospecific capture of ligands, retained within the confines of the individual interactive surfaces. The IA sensor chip is then prepared for laser desorption/ionization mass spectrometry by, for example, application of a MALDI matrix (if necessary), and associated with a mass spectrometer. Mass spectrometry then follows with the retained ligands detected at precise and characteristic m/z values.

Association of the IA sensor within the mass spectrometer may be achieved by a variety of techniques. For example, the IA sensor may be affixed to the end of a probe for insertion into the mass spectrometer as discussed in greater detail below (which was the technique employed to generate the SPR-MS of Examples 1–2 and 4–7). Since the probe is inserted into the interior of the mass spectrometer through a series of seals, the interior of the spectrometer remains under vacuum. In the practice of this invention, association of the interactive surface(s) of the IA sensor with the interior of the mass spectrometer such that vacuum within the mass spectrometer is not lost, or only minimally affected, is preferred. Alternatively, the interior of the mass spectrometer may be brought to atmospheric pressure, and the IA sensor placed directly therein. A vacuum is then reestablished within the interior of the mass spectrometer (which was the technique employed to generate the data of Examples 3 and 8).

A variety of methods, including sample pins, probes, plates, carousels, disks and the sensor chip itself, may be utilized for association of the IA sensor with a mass spectrometer. Manipulation of the sensor within the vacuum system may be accomplished through one-, two-, or three-dimensional translation, as well as rotary motion. Alternatively, targeting of individual sample spots on the sensor (different flow cells, for instance) can be accomplished by stationary placement of the sensor in the mass spectrometer and directing the desorption/ionization source (e.g., laser light, ion or atom beam) at the individual areas.

With regard to IA sensor chips, the surface of the chip having the analyte captured thereon may be located against appropriate seal(s) such that the surface is within the mass spectrometer, while the surrounding edges of the same are in contact with the seal(s) as such to maintain vacuum within the mass spectrometer. The conductive layer of the SPR sensor chip can then be biased, relative to extraction electrodes placed within the mass spectrometer, through appropriate points of electrical contact. The sensor chip in this case serves a three-fold purpose: as the IA sensor; as the sample source (stage) in the mass spectrometer; and as part of the vacuum housing of the mass spectrometer.

A representative device for this purpose is illustrated in FIG. 5. Specifically, FIG. 5A is a cross-sectional view of insulating flange (510) sealed to vacuum chamber wall (540) of a mass spectrometer via seal (512). Electrodes (544) are internally located within the mass spectrometer. IA sensor chip (520) is affixed to chip carrier (522) having apertures sized to accept guide pins (530). Shutter valve (550) is movably affixed within insulating (i.e., non-conductive) flange (510) such that the interactive surface layer (524) of chip (520) is located within the interior of the mass spectrometer when the shutter valve is in an "open" position as illustrated in FIG. 5A. When shutter valve (550) is in a "closed" position, as illustrated in FIG. 5B, vacuum is maintained within the interior of the mass spectrometer when sensor chip (520) affixed to chip carrier (522) is removed from contact with flange (510). An appropriate desorption/ionization source, such as a laser light (560) (i.e., front side) or (561) (i.e., back side) is directed to contact interactive surface layer (524) as illustrated in FIG. 5A. FIG. 5C is an enlarged view of sensor chip (520) affixed to chip carrier (522), and seals (514) which contact sensor chip (520) and insulating flange (510) to maintain vacuum within the mass spectrometer. FIG. 5C also illustrates placement of gridded electrode (580) with electrical contact (582), and contact surfaces (584) in electrical contact with both the conductive material on the surface of sensor chip (520) and with electrical contact (586). In this manner, a potential can be placed between electrical contacts (582) and (586) (e.g., 20 kV/cm) to directionally assist passage of ions into the mass spectrometer. FIG. 5D is a top view of sensor chip (520), chip carrier (522), insulating flange (510) and guide pins (530).

Figure 6:
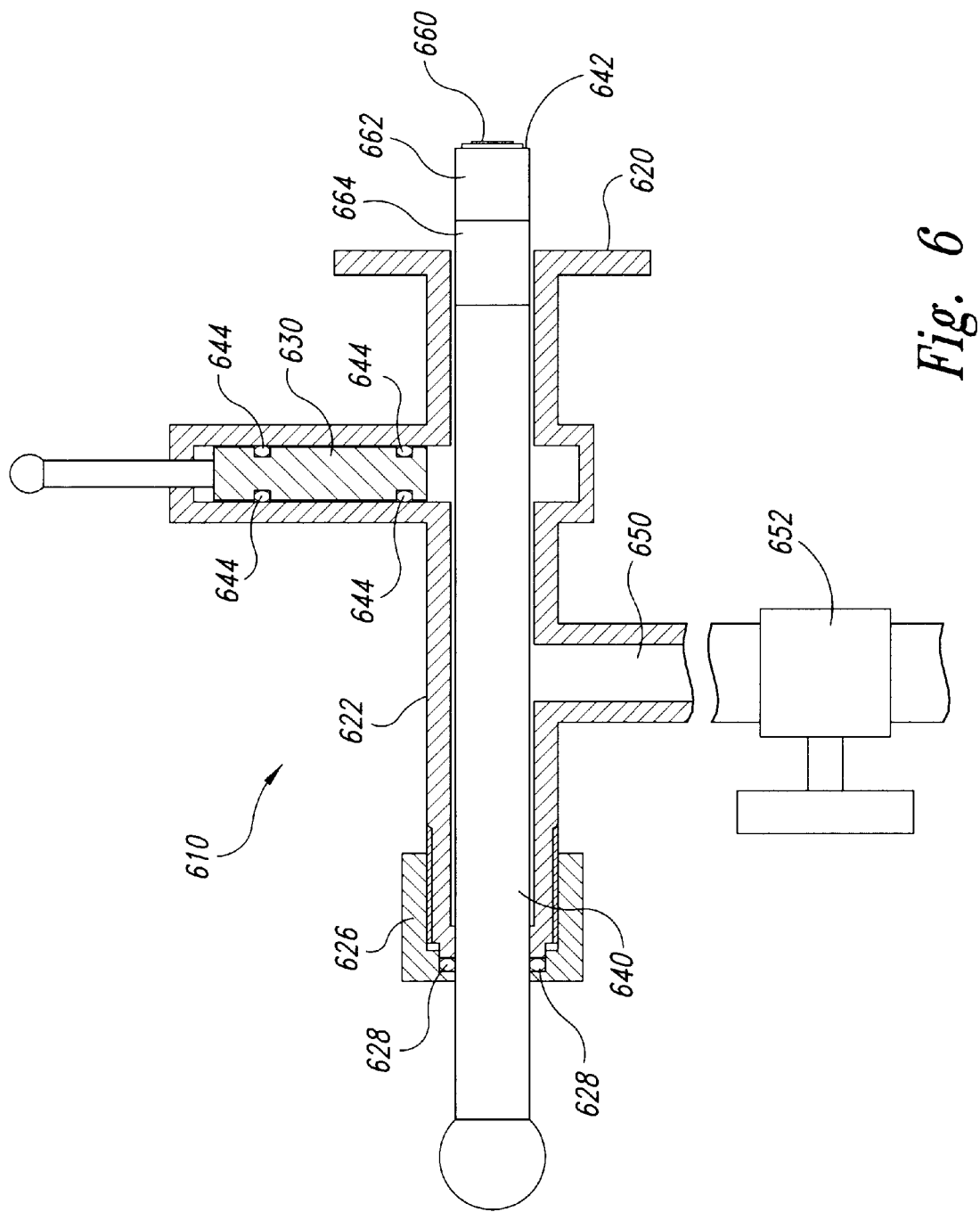
FIG. 6 illustrates a representative probe insertion device for introduction of an IA sensor into the interior of a mass spectrometer.

A further representative device suitable for insertion of an IA sensor into a mass spectrometer is illustrated in FIG. 6. IA sensor insertion device (610) has flange (620) for connection to a mass spectrometer (not shown) and tubular portion (622) for accepting mass spectrometer probe (640). High vacuum valve (630) when in the open position (as shown in FIG. 6) permits passage of probe tip (642) into the interior of the mass spectrometer, and when in a closed position (not shown) maintains the vacuum within the interior of the mass spectrometer with the aid of seals (644). When inserting probe (640) through seal tightening nut (626) and vacuum seals (628), high vacuum valve (630) is initially in the closed position, and probe (640) is inserted such that probe tip (642) is in close proximity to high vacuum valve (630). A partial vacuum is then drawn through port (650) via a rough vacuum pump (not shown) and vacuum valve (652). High vacuum valve (630) is then opened, and probe (640) is inserted to its full length such that probe tip (642) is located within the interior of the mass spectrometer. An IA sensor, which in FIG. 6 is illustrated as IA sensor chip (660), is attached to holder (662) which, in turn, is attached to insulator (664) of probe (640).

In the case of a fiber optic IA sensor, the fiber optic may be affixed to the end of a probe as illustrated in FIG. 6 and introduced into the mass spectrometer. Alternatively, and in a preferred embodiment, the portion of the fiber optic having the analyte captured thereon may be inserted into the interior of the mass spectrometer through a series of airtight seals. Desorption/ionization methods may then be applied with the fiber optic device serving as the sample stage.

Regardless of the insertion technique, the interactive surface of the SPR sensor having the analyte captured thereon must be physically located within the interior of the mass spectrometer such that the desorbed/ionized analyte can be detected by the mass spectrometer. Furthermore, in a preferred embodiment, the conductive material capable of supporting SPR is electrically connected to apparatus of the mass spectrometer (e.g., high voltage sources or ground) to create an electrostatic "accelerating" field between the sensor surface and extraction electrodes within the mass spectrometer. The extraction field may be applied continuously during the desorption/ionization event, or at some time thereafter (delayed).

A first criterion to performing mass spectrometry on the analyte captured by the interactive surface is the generation of vapor-phase ions. In the practice of this invention, such species are generated by desorption/ionization techniques. Suitable techniques include desorption/ionization methods derived from impact of particles with the sample. These methods include fast atom bombardment (FAB—impact of neutrals with a sample suspended in a volatile matrix), secondary ion mass spectrometry (SIMS—impact of keV primary ions generating secondary ions from a surface), liquid SIMS (LSIMS—like FAB except the primary species is an ion), plasma desorption mass spectrometry (like SIMS except using MeV primary ions), massive cluster impact (MCI —like SIMS using large cluster primary ions), laser desorption/ionization (LDI—laser light is used to desorb/ ionize species from a surface), and matrix-assisted laser desorption/ionization (MALDI—like LDI except the species are desorbed/ionized from a matrix capable of assisting in the desorption and ionization events). Any of the aforementioned desorption/ionization techniques may be employed in the practice of the present invention. In a preferred embodiment, LDI is employed, and in a more preferred embodiment, MALDI is utilized.

With regard to MALDI, laser energy is impinged upon the surface of the IA sensor, resulting in the desorption/ionization of the captured analyte. The ionized analyte is then detected by the mass spectrometer. In one embodiment of this invention, the laser is directed to the surface of the IA sensor having the analyte captured thereon. In an alternative embodiment, the laser may be directed to the back side of the IA sensor. In the case of an IA sensor chip, the laser may be directed through the transparent material such that it strikes the backside of the metal layer in contact with the captured analyte. In the case of a fiber optic IA sensor, the laser may be coupled into the end of the fiber optic for backside desorption/ionization.

Furthermore, when multiple interactive surfaces are employed on a single IA sensor, the laser may be directed to a single interactive surface. In this manner, the captured analyte from a single surface may be analyzed by mass spectrometry. When the desired mass spectral data is collected from a particular surface, the laser may then be directed to the next surface for analysis. In this manner, the mass spectrum of analytes captured by the IA sensor may be individually addressed. This is particularly advantageous when each of the interactive surfaces provides different information concerning the analyte or analytes within the sample, or provides further confirmation that the analyte is present within the sample of interest.

The following examples are offered by way of illustration, not limitation.

EXAMPLE 1

Surface Plasmon Resonance-Mass Spectrometry

Figure 7A:
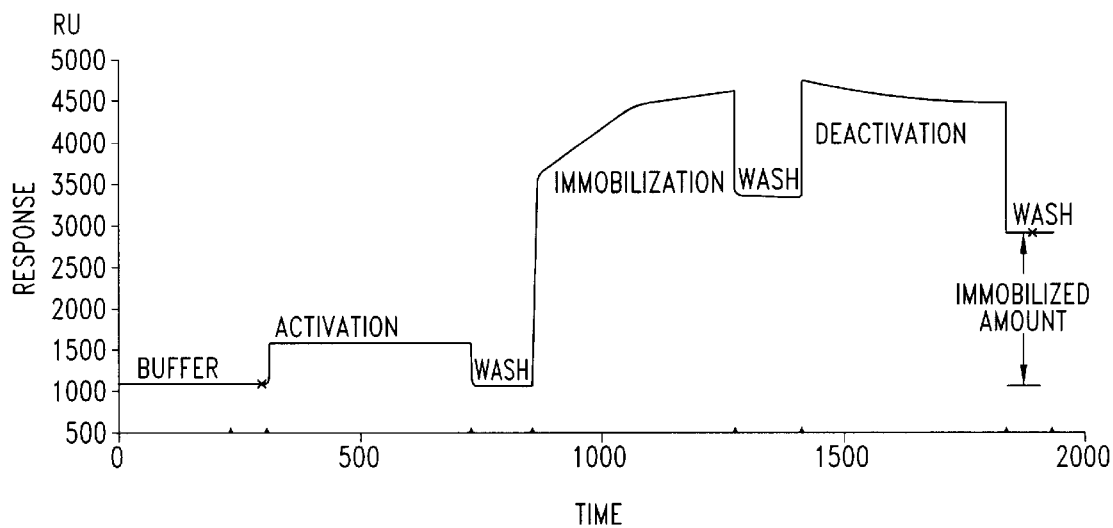
Figure 7B:
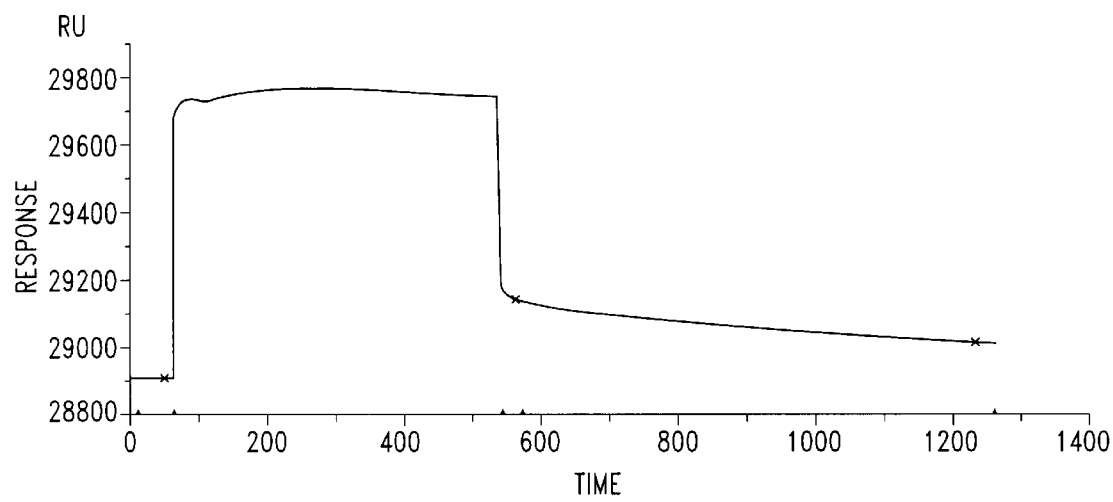
FIG. 7B is a sensorgram illustrating the real-time binding of myotoxin a from whole C.v. viridis rattlesnake venom within an anti-myotoxin a derivatized flow cell (a SPR signal of 100 RU corresponds to ~40 fmole protein retained on the surface of the BIAcore chip).

SPR-MS analysis was performed on a Pharmacia Biosensor BIAcore 2000 using a CM5 chip (carboxylated dextran surface) derivatized with anti-myotoxin a polyclonal IgG following an EDC/NHS coupling protocol (Johnsson et al., *Anal. Biochem.* 198:268–277, 1992). FIG. 7A shows the sensorgram of the anti-myotoxin a immobilization process (sensorgram of one flow cell). Signal plateaus are observed at ~6 and 15 minutes. The first stems from the incubation of the NHS-activated sensor chip surface with anti-myotoxin a IgG (flow rate=10 µL/minute, 1 µg/mL in binding buffer: 20 mM Hepes, 0.005% Tween 20, 150 mM NaCl, 5 mM EDTA, pH 7.4 (HBS)). The surface was then flow washed for ~2.5 minutes. The second plateau represents the blocking of remaining reactive NHS sites with ethanolamine (10 µL/minute, 1 µg/mL). After blocking, a net change in response of ~20,000 RUs was indicated. This number corresponds to ~150 fmol/mm$^2$ of anti-myotoxin a IgG covalently coupled to the chip, which in turn represents a maximum surface binding activity towards myotoxin a of ~300 fmol/mm$^2$ (assuming that all the IgG is oriented correctly for antigen binding). Whole venom solution (1 µg/mL in HBS) from the prairie rattlesnake, *Crotalus viridis viridis,* was circulated across the flow cell for ~8 minutes (10 µL/minute). The flow cells was then rinsed for ~12 minutes with HBS. FIG. 7B shows the resulting sensorgram. The ΔRU value of 100 corresponds to ~40 fmole of myotoxin a bound to the entire cell surface. This value is somewhat less than the expected saturation level (~300 fmole) suggesting a number of possibilities, including too short an incubation time (a reflection of the molar absorptivity of the antibody), or that the orientation of the antimyotoxin a on the dextran surface was not optimal for antigen binding.

Figure 8:
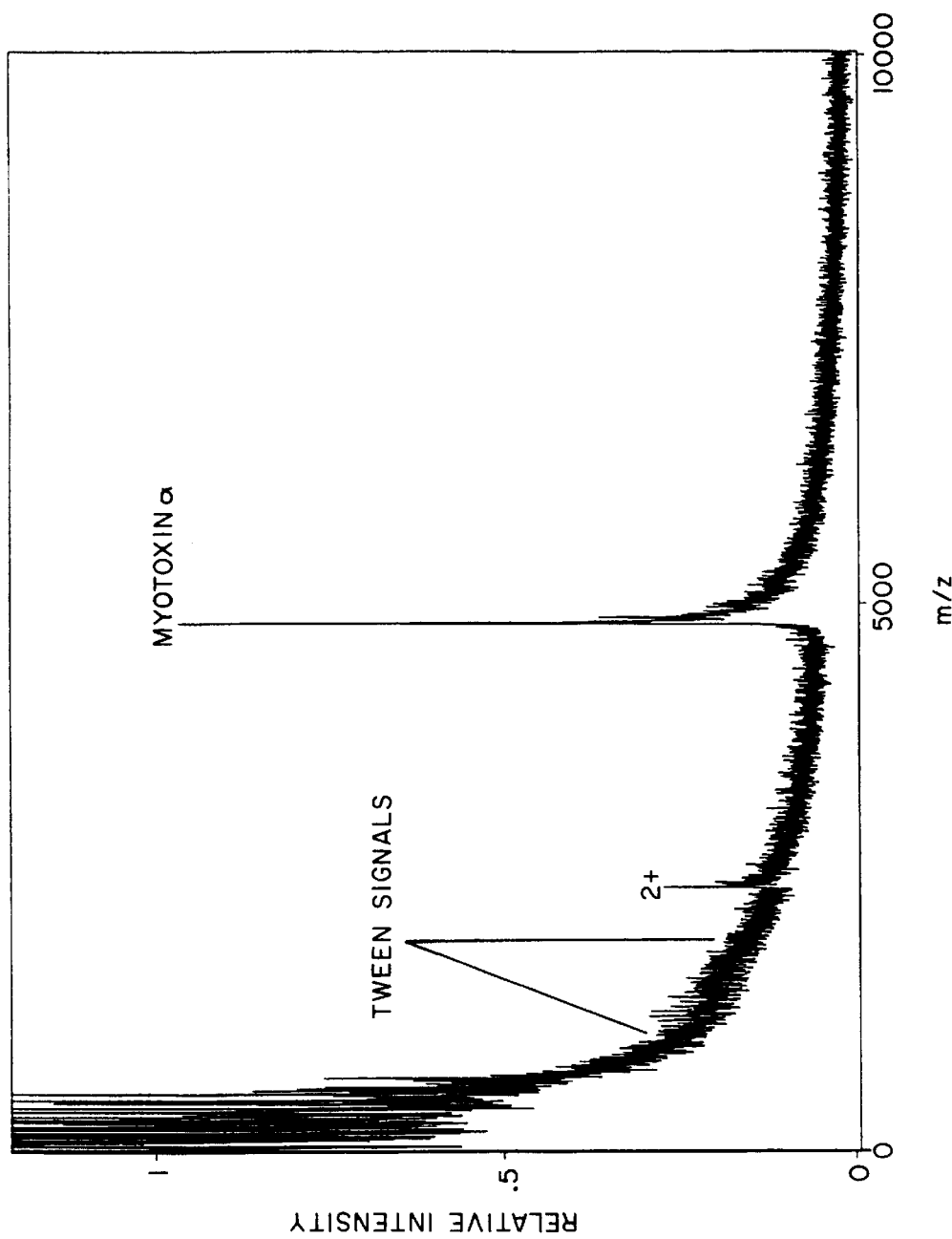
FIG. 8 is the SPR-MS spectrum of myotoxin a (m/z=4, 823 Da) retained within one flow cell of a BIAcore chip which was previously monitored and analyzed by SPR as illustrated in FIG. 7B.

The BIAcore chip was then removed from the Biosensor unit with the ligands still bound to the surface. Approximately 100 nL of a MALDI matrix, α-cyano-4-hydroxycinnamic acid, (~50 mM in 1:2, acetonitrile: 1.4% TFA (ACCA)) was then carefully applied within the confines of the flow cell and allowed to air dry. MALDI analysis was performed on the chip using a linear time-of-flight mass spectrometer equipped with a pulsed, frequency-tripled Nd:YAG laser (λ=355 mn) and a 30 kV acceleration stage. FIG. 8 is the SPR-MS spectrum resulting from targeting the flow cell. Signals due to the singly- and doubly-charged ions of the myotoxin a are observed as the major species present in the spectrum (m/z=4,823 and 2,412 Da, respectively). A minor polymeric component is observed in the m/z=1–2 kDa region, presumably resulting from residual detergent (present in the HBS). The unambiguous identification of the myotoxin a is not hindered by the presence of the detergent signals (because the signals register at resolved masses), however, the quantitative estimation of the myotoxin a present on the chip surface from the SPR signal (~100 RU) may not be completely accurate as the SPR detection does not discriminate between the two species. Regardless, both methods of detection, SPR and MS, exhibit comparable detection limits and S/N ratios indicating high compatibility and complementarity.

This example demonstrated that MALDI time-of-flight mass spectrometry can be readily coupled to SPR-based interaction analysis (IA) without deleterious effect to either of the techniques. SPR analysis provides a means of first characterizing the affinity ligand-derivatized sensor surface, then quantifying the targeted affinity interaction. Mass spectrometry adds immediate specificity to the IA analysis, together with the potential for improved quantitation due to the identification of interfering absorbates. The combined technologies allow for the rapid, sensitive and accurate investigations of molecular interactions.

EXAMPLE 2

Incorporation of Internal Reference Species

SPR-MS analyses were performed as describe in Example 1 above. Three of the four flow cells of a CM5 chip were derivatized with polyclonal anti-myotoxin a IgG to levels of ~20,000 RU. All four flow cells were then addressed for 10 minutes with 1 mg/mL *C.v. viridis* whole venom (flow rate=10 µL/minute), to create saturating conditions (i.e., the antibody was fully loaded with myotoxin a—~150 fmole per derivatized flow cell). A matrix (ACCA) solution containing 0.01 mg/mL angiotensin II (MW=1046.2) was applied to flow cells 1 and 3. A different matrix solution containing 0.01 mg/mL secretin (MW=3039.5) was applied to flow cells 2 and 4.

Figure 9:
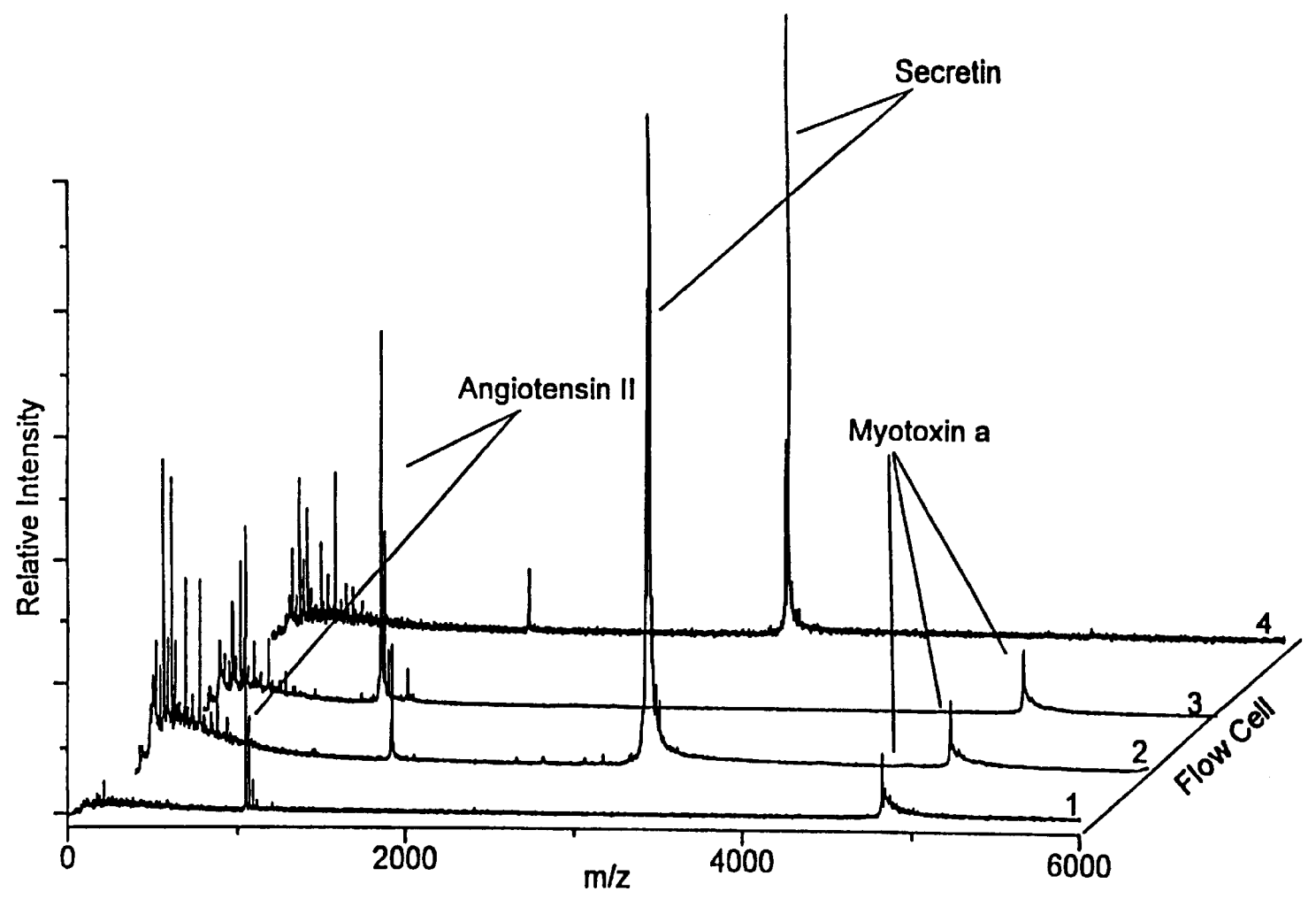

FIG. 9 shows the SPR-MS spectrum for each of the individual flow cells. Both myotoxin a (retained by the antibody during SPR analysis) and angiotensin II (added with the matrix) are observed in spectra obtained from flow cells 1 and 3. Myotoxin a (retained) and secretin (added) are observed in the spectrum obtained when flow cell 2 was targeted, whereas only secretin is present in the mass spectrum from flow cell 4. This observation, lack of myotoxin a in flow cell 4, is consistent with the flow cell 4 not being derivatized with antibody during the sample preparation.

The different peptide-labeled matrix solutions were applied for the primary purpose of unambiguously verifying the identity of each flow cell when targeted with the laser. The peptide signals, however, can serve other purposes beyond signature of the spatial location of the laser spot. The first of these is use as an internal mass calibrant. Knowing the molecular weight of the reference peptides, it is possible to use the flight times of their ion signals to generate a highly accurate time-of-flight to m/z conversion equation, and then apply the equation to the flight times of the analyte ions to achieve an accurate (~0.02%) determination of the (analyte) molecular weight. Another use of the peptide signals is that of internal reference standard for quantitative analysis. The internal reference species is used for signal normalization in order to compensate for variations in instrumental response which may be experienced between different sample (due to different laser irradiances or sample condition). In this particular example, the angiotensin II signal serves as an internal reference species to compare the myotoxin a signals of flow cell 1 and 3. A marginally greater (~20%) amount of myotoxin a is indicated for flow cell 1 (myotoxin a/angiotensin II=0.20 vs. 0.16 for flow cell 3). Further, absolute quantitation is possible using the same method (within a given concentration range) by establishing the relative molar responses of the two ion species, the relative response then equated to an analyte concentration.

This example this illustrates the ability to incorporate reference species into the SPR-MS technique to (1) verify the identity of the targeted sample area, and (2) calibrate both the x- (m/z) and y-axis (relative ion signal) for accurate mass determination and quantitation, respectively.

EXAMPLE 3

Recognition of Competitive and Non-Specific Binding

SPR-MS analyses were performed on a rabbit anti-human IgG/human myoglobin system using a Pharmacia Biosensor BIAcore 2000 (Uppsala, Sweden). Individual flow cells of CM5 (carboxylated dextran) sensor chips were derivatized with polyclonal rabbit anti-human IgG using the amine-coupling protocol described in Example 1. Cyano-stabilized human myoglobin (400 ng/mL) in the presence of human serum albumin (90 mg/mL) was flowed (10 µL/minute; 20 mM HEPES, 0.005% Tween 20, 150 mM NaCl, 5 mM EDTA, pH 7.4 (HBS)) over the anti-myoglobin-derivatized flow cells for times ranging from 30 second to 3 minutes while monitoring the SPR signal. After incubation, the flow cell surfaces were (flow) rinsed with HBS for an additional 3 minutes before the chips were de-blocked from the instrument. Chips were dried and stored at ambient temperature until mass spectrometric analysis. Approximately 100 nL of a MALDI matrix, α-cyano-4-hydroxycinnamic acid, (~50 mM dissolved in 1:2, acetonitrile: 1.4% TFA) was applied to each of the four flow cells (500 mm×2.0 mm) and allowed to air dry. The chips were next introduced into a MALDI time-of-flight mass spectrometer and mass spectrometry performed with each flow cell targeted individually.

Figure 10A:
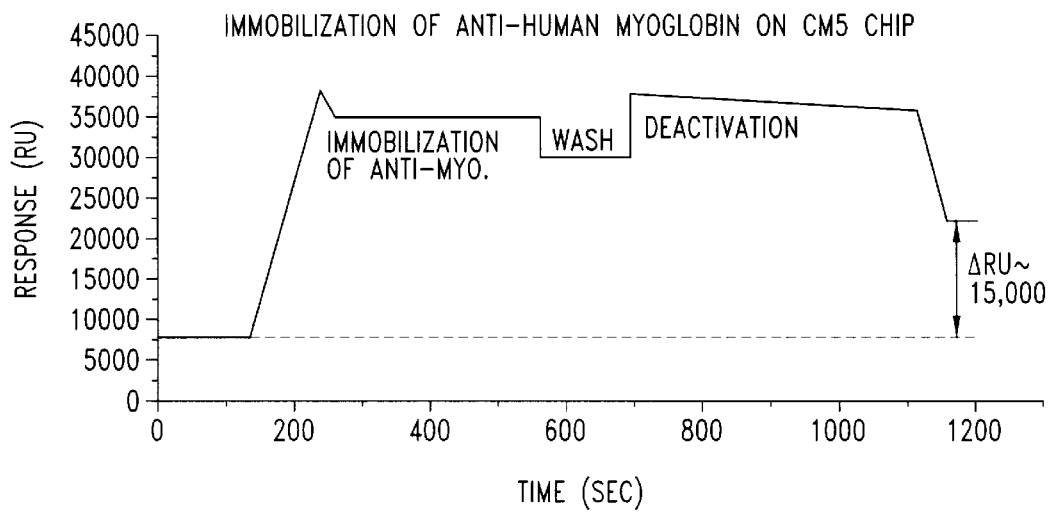
FIG. 10A is a sensorgram illustrating anti-human myoglobin IgG immobilization within one flow cell of a BIAcore CM5 chip. A reading of $\Delta RU=15,000$ is indicated and corresponds to a binding capacity of ~200 fmole myoglobin.
Figure 10B:
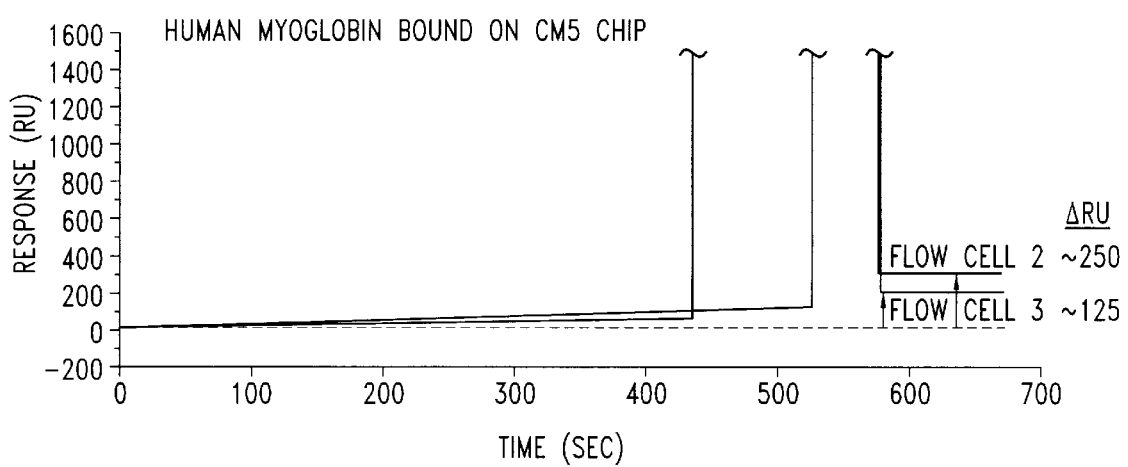
FIG. 10B is a sensorgram illustrating the binding of human myoglobin, in the presence of HSA (20 mg/mL), within flow cells 2 and 3 on a CM5/anti-human myoglobin IgG derivatized BIAcore chip. Retention of 20 fmole ($\Delta RU=250$), and 10 fmole ($\Delta RU=125$), of myoglobin is indicated for flow cells 2 and 3, respectively.

A sensorgram of the antibody immobilization is given in FIG. 10A. Anti-human IgG (~2 mg/mL in HBS) was flow incubated over the chip surface for ~7 minutes before a ~2 minute rinse with HBS, followed by an ~7 minute incubation with ethanolamine (blocking agent). The final response difference in the sensorgram, a reading of ~15,000 RU, translates to ~15 ng of antibody covalently linked to the surface of the 1 $mm_2$ area of the flow cell. Considering two binding sites per antibody molecule, a myoglobin binding capacity of 200 fmole is estimated for the flow cell. All four flow cells of the sensor chip were derivatized using identical conditions and resulted in virtually identical sensorgrams (i.e., <1% deviation in the amount of antibody bound). FIG. 10B shows sensorgrams obtained during the incubation of the anti-myoglobin-derivatized flow cells with human myoglobin. Sensorgrams for flow cells two and three are shown. A difference in the sensorgram signal of ~250 RU translates to approximately 0.25 ng of material (~20 fmole of myoglobin) retained in flow cell 2 (during the 2.5 minute incubation). The sensorgram signal for flow cell 3 indicates roughly half that amount (~0.125 ng; ~10 fmole myoglobin) retained during the shorter incubation time (1 minute).

Figure 11:
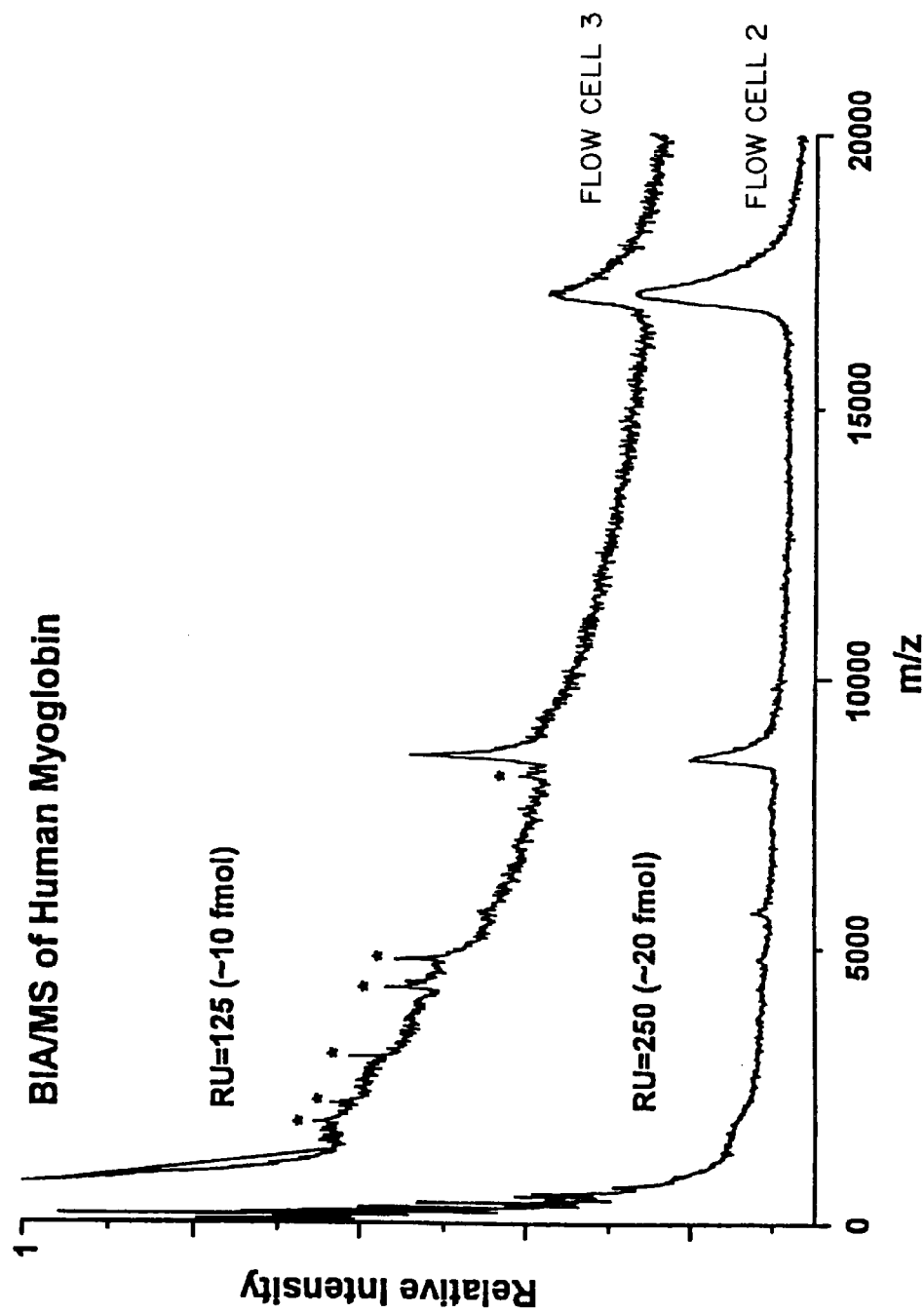
FIG. 11 illustrates SPR-MS spectra of the CM5/anti-human myoglobin IgG/myoglobin system retained on flow cells 2 and 3 of FIG. 7B. Myoglobin is present at m/z~17, 150 Da, along with several lower molecular weight species (indicated by asterisks).

FIG. 11 shows the mass spectra obtained from the direct MALDI-TOF analysis of flow cells 2 and 3. FIG. 11 (lower) was one of ca. 5 mass spectra taken from the area within flow cell 2. Significant signal is observed for both the singly- and doubly-charged ion species of the myoglobin. A measured molecular mass of 17,150±15 Da was found for the myoglobin by averaging the centroided mass values of the 5 spectra acquired from flow cell 2. This molecular weight is significantly higher (~0.4%) than that calculated for the mono-derivatized (cyano)myoglobin (MW=17,080 Da). Considering that the myoglobin ion signals are fairly broad, the shift to higher mass is consistent with the attachment of multiple cyano groups to the myoglobin (creating a heterogeneous sample). FIG. 11 (upper) shows a mass spectrum obtained from within flow cell 3. From the sensorgram it may be estimated that ~10 fmole of myoglobin was present within the area of the flow cell. Again ion signal is readily observed for the myoglobin. A measured mass of MW=17160±15 Da was determined for the myoglobin using the average of ca. 5 mass spectra taken from within the area of flow cell 3.

Based on these results, a few issues relating to SPR-MS are worth noting. The first is the comparable sensitivities of the two techniques. IA analyses registering above the ~100 RU level are generally considered significant. This sensorgram response translates to ~5 fmole of a 20 kDa protein retained over an area of ~1 $mm^2$ (the area of a flow cell), an amount generally considered at the limit of detection of MALDI-TOF analysis. Furthermore, the overall sensitivity of the SPR-MS (analysis of retained analytes directly from the IA sensor) is not compromised by sample losses associated with eluting the retained affinants and transfer to the mass spectrometer. In fact, there was no actual handling of the samples for mass spectrometry beyond the simple application of a MALDI matrix solution to the IA sensor surface. A second aspect of the SPR-MS analysis is the observance of species in the mass spectra other than those targeted. Spectra obtained from flow cell 3 exhibited the presence of a number of lower molecular weight species retained along with the myoglobin (marked by *). Blank analyses of flow cells derivatized with antibody and incubated with HBS/HSA buffer (no myoglobin) demonstrated the presence of a number of the lower molecular weight species, however, not all those observed in flow cell 3. A combination of both non-specific retention of background species, and specific retention of myoglobin fragments (present in the starting solution) is suggested. Non-specific retention (while of obvious concern) can be identified and compensated for during IA analysis by blank subtraction or saturation of the sensor chip surface (with non-specific agents). It is not easy, however, to compensate for the specific binding of non-targeted ligands while simultaneously analyzing for targeted ligands. By direct detection of retained species at defined molecular weights and incorporation of quantitative methodologies, SPR-MS may be used to evaluate such competitive binding.

This example thus demonstrates the use of SPR-MS to semi-quantitatively evaluate a molecular interaction analysis, and to rapidly recognize qualitative differences in analyses due to various degrees of non-specific retention, and competitive binding.

EXAMPLE 4

Small Molecule-Neat Laser Desorption/Ionization

Figure 12A:
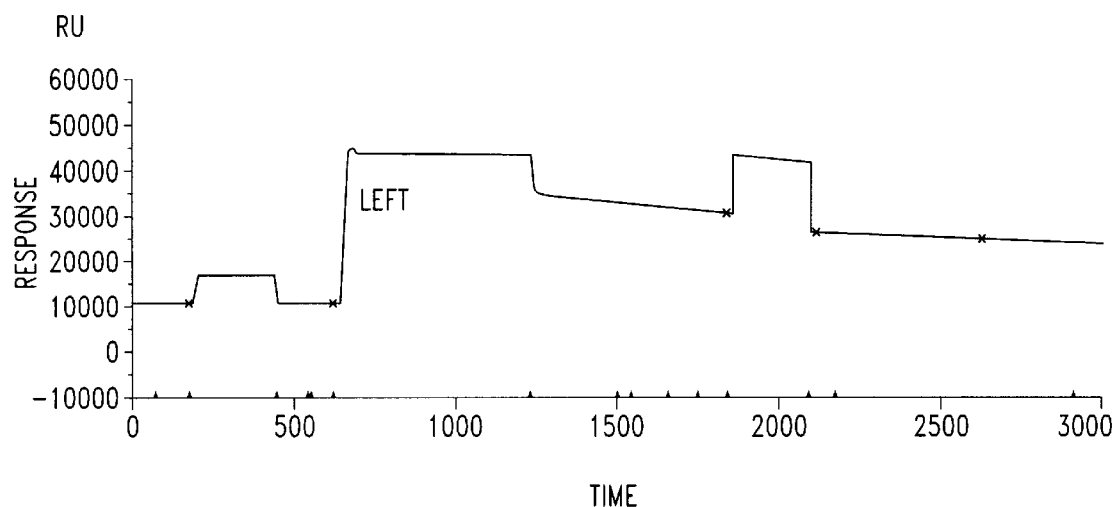
FIG. 12A is a sensorgram of CM5/anti-clenbuterol IgG immobilization. A reading of $\Delta RU=17,000$ is indicated and corresponds to a binding capacity of ~200 fmole clenbuterol.
Figure 12B:
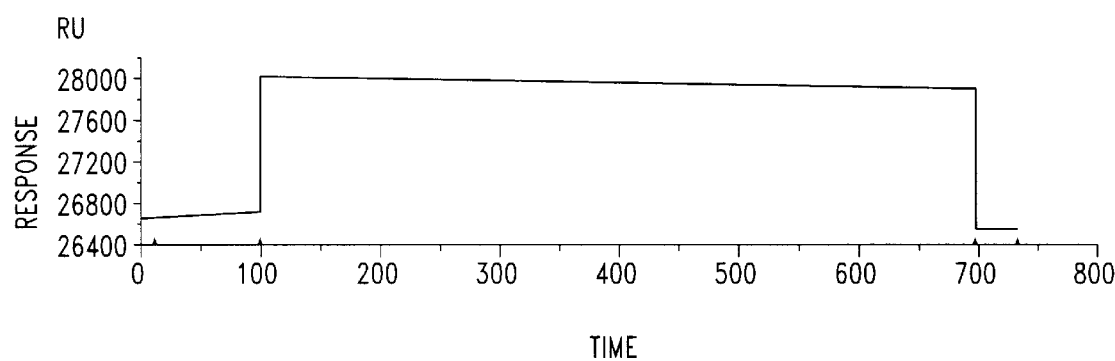
FIG. 12B is a sensorgram illustrating the binding of clenbuterol, spiked in calf urine at a concentration of 50 ppb, to one flow cell (flow cell 4) of a CM5/anti-clenbuterol IgG derivatized BIAcore chip (SPR response levels having reached the limit of detection).

Flow cells of a CM5 chip were derivatized with monoclonal anti-clenbuterol IgG to a surface concentration level of ~17,000 RU (17 ng/mm$^2$) while the immobilization process was monitored using IA detection (FIG. 12A). Calf urine, spiked to contain 50 ppb clenbuterol (a di-chlorinated steroid with an average chemical mass of 277.2 Da), was then flowed for 10 minutes (10 μL/minute) across the antibody-derivatized flow cells, again while monitoring with IA. IA response levels at the limit of detection were experienced yielding ambiguous determination of the clenbuterol (FIG. 12B).

Figure 13:
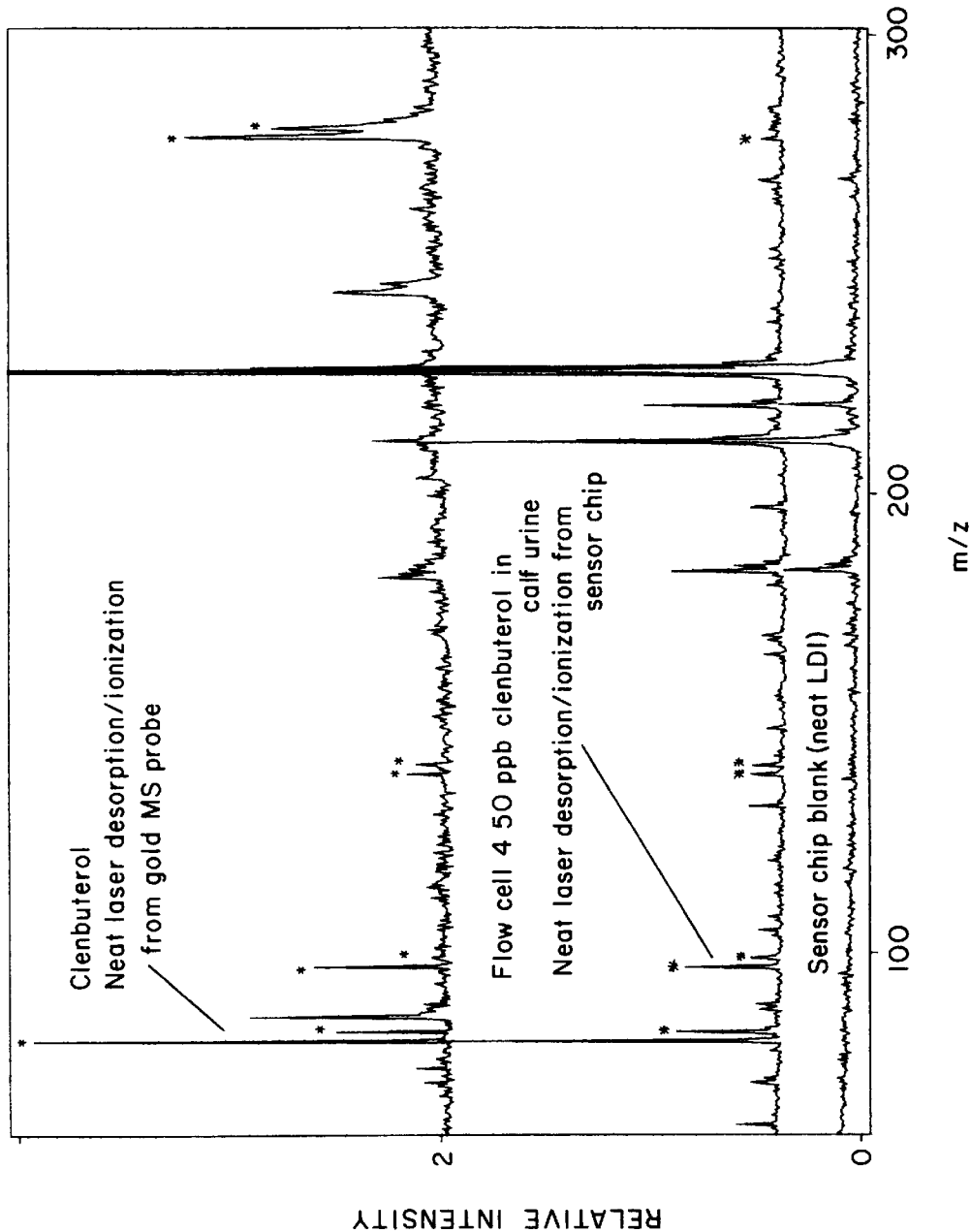
FIG. 13 is a neat (i.e., no MALDI matrix) SPR-MS spectrum (middle) of flow cell 4 of the CM5/anti-clenbuterol/clenbuterol system of FIG. 9B. For comparison, spectra of the neat laser desorption/ionization of clenbuterol from a gold-coated mass spectrometer probe tip (top) and of an underivatized sensor chip (bottom) are also presented. Ion signals characteristic of the clenbuterol are marked with asterisks.

Laser desorption/ionization time-of-flight mass spectrometry was performed directly from the sensor chip with no further sample preparation (this is a process typically referred to as "neat" sample preparation). FIG. 13 (middle) shows a SPR-MS obtained from a single flow cell of the anti-clenbuterol/clenbuterol sensor chip (flow cell 4—exposed to 50 ppb clenbuterol in calf urine). For comparison, spectra (upper) of clenbuterol desorbed/ionized from an ordinary, gold-plated mass spectrometer probe tip (clenbuterol, neat off gold probe tip), and spectra (lower) of an underivatized sensor chip are given (chip blank). Ion signals characteristic of the clenbuterol are marked (*) in the comparison spectrum. Signature signals separated by 2 Da—the mass difference between the chlorine isotopes (35 and 37 amu)—are easily observed throughout the clenbuterol spectrum, as well as the spectrum obtained from flow cell 4. The blank spectrum shows a few common background signals, but none within the signature region of the clenbuterol.

Demonstrated in this example is the necessity of the two techniques, IA and mass spectrometry. IA response signals at the limit of detection were experienced during incubation of clenbuterol-spiked calf urine with an antibody-derivatized flow cell. The integrity of the affinity surface, however, could not be questioned due to the continuous monitoring of the immobilization process, and verification of the presence of sufficient antibody, using IA (FIG. 12A). The limit of IA detection is reached purely because of the low molecular weight of the analyte species. For instance, it is necessary to retain ~30 fmole of clenbuterol in order to generate an IA signal of 10 RU (the practical limit of detection). Anything less is not considered significant signal for analyte determination. Thirty fmoles of clenbuterol is, however, ample material for mass spectrometric analysis (neat laser desorption/ionization is possible with attomole quantities of sample). As such, SPR-MS signals characteristic of the clenbuterol are readily observed during the direct (neat) laser desorption/ionization mass analysis.

EXAMPLE 5

Background Subtraction

SPR-MS analyses were performed to investigate the biospecific interaction between a tri-peptide, QPH, and streptavidin, using a Biosensor instrument with all four flow cells in contact with a streptavidin-derivatized (SA5) sensor chip. Flow cells were monitored as either E. coli lysate, or lysate spiked to contain 10 mg/mL of the dimerized peptide NH$_2$-SSFQPHWLC (dimer MW=2,206.4 Da; referred to as "P1") were continuously infused (in HBS) at a flow rate of 10 μL/minute. After an ~3 minute incubation, the flow cell were flow rinsed with HBS for ~5 minutes before removal of the sensor chip from the Biosensor instrument. MALDI time-of-flight mass spectrometry was performed as described in Example 1 with each of the flow cells targeted individually.

Figure 14:
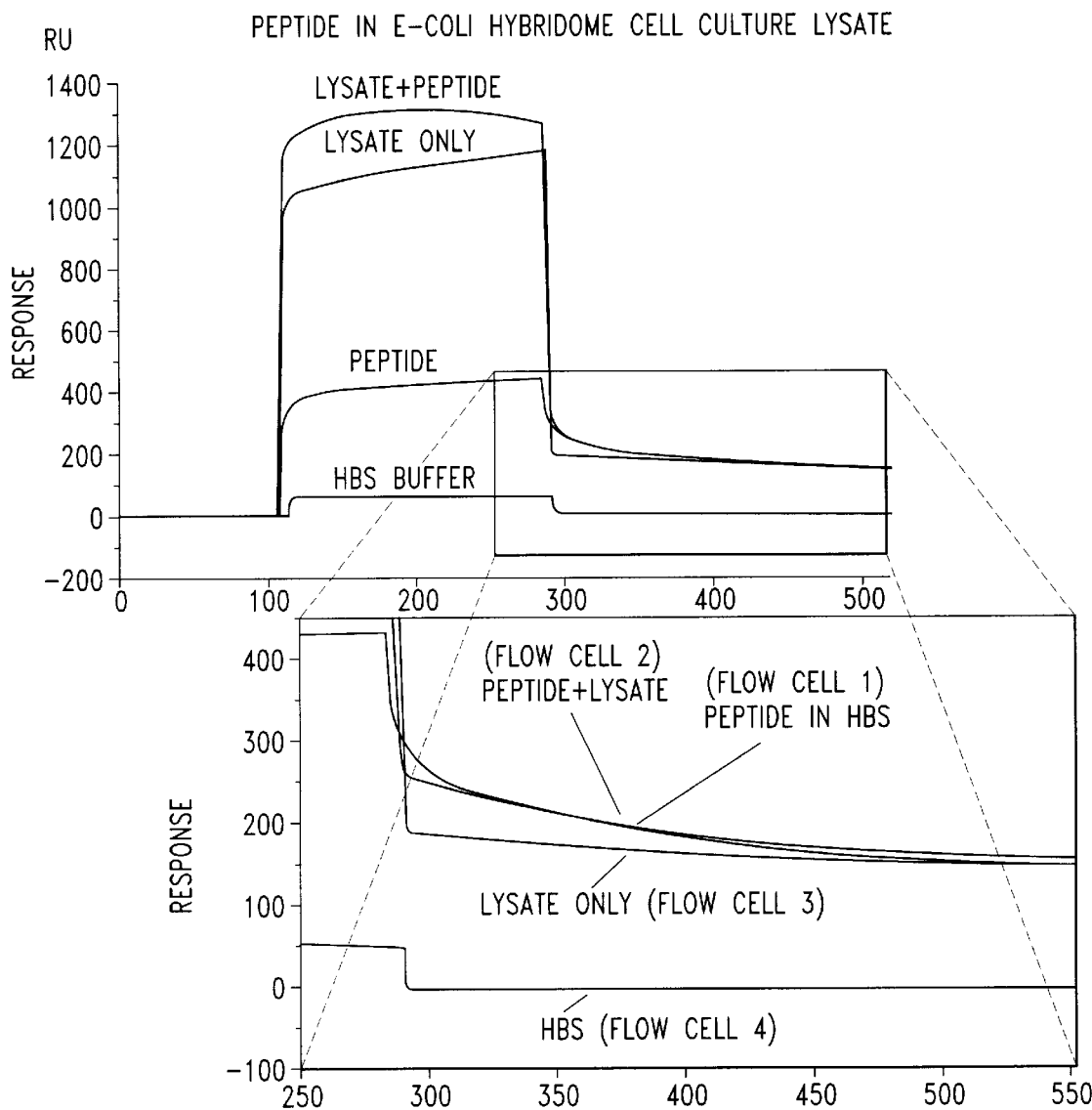
FIG. 14 is a sensorgram of a SA5/streptavidin/HPQ peptide system illustrating binding within all four flow cells of a streptavidin BIAcore chip. Flow cell 1 contains the HPQ peptide in HBS; flow cell 2 contains the HPQ peptide doped in cell lysate; flow cell 3 contains only the cell lysate; and flow cell 4 contains only the HBS. An SPR signal of ~100 RU in flow cells 1 and 2 corresponds to ~50 fmole of peptide retained. Flow cell 3, which does not contain any of the peptide, also has an SPR reading of ~100 RU (i.e., there is a response difference between background and sample).
Figure 15:
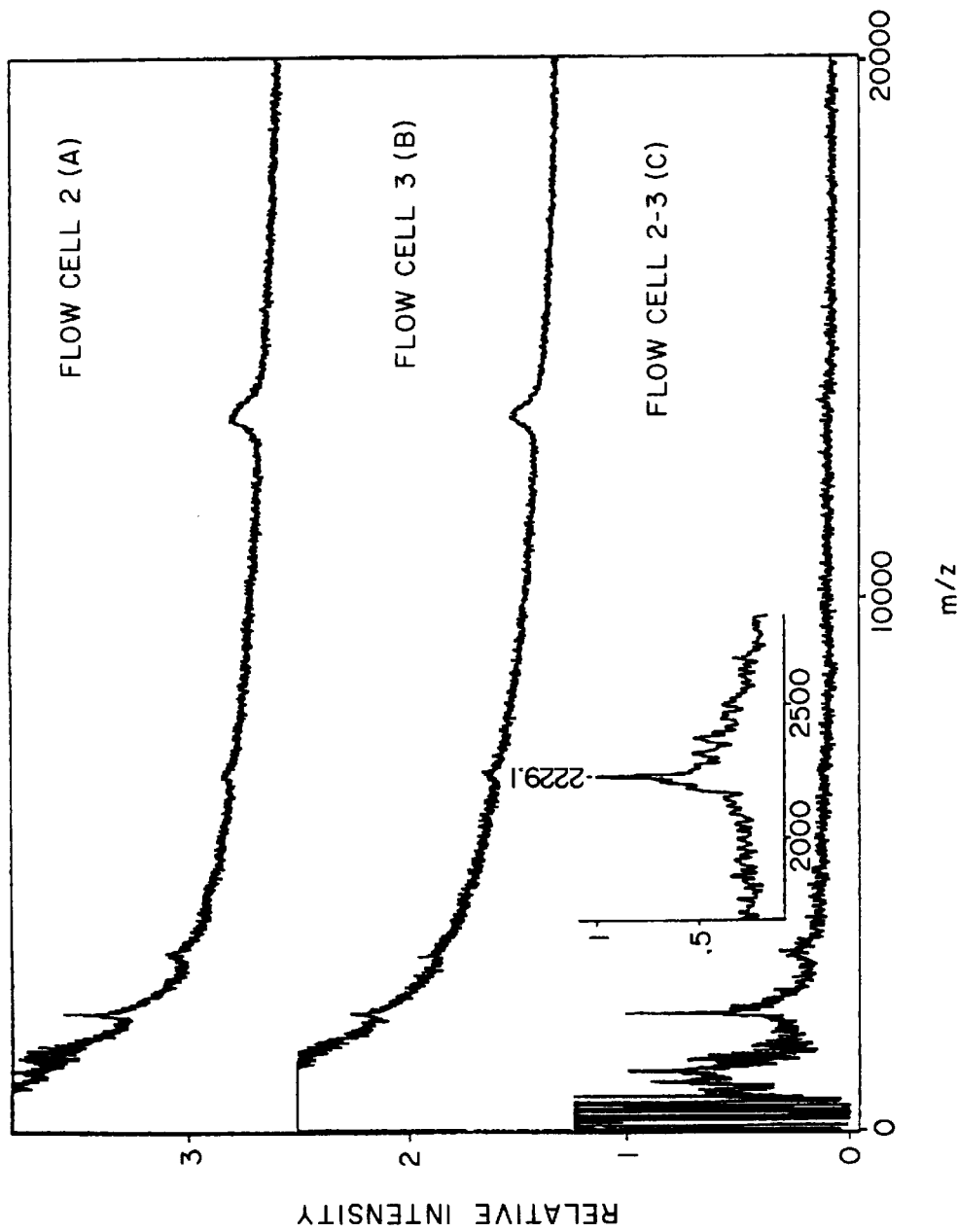
FIG. 15A is a SPR-MS spectrum of the SA5/streptavidin/ HPQ peptide-cell lysate system retained in flow cell 2. Signals due to the singly- and doubly-charged avidin are observed at m/z~13,000 Da and 6,500 Da, respectively. The peptide is detected as a disulfide-linked dimer at m/z~2229 Da (representing the sodiated peptide).
FIG. 15B is a SPR-MS spectrum of flow cell 3 of the SA5/streptavidin/cell lysate system. This spectrum is used as a background since it does not contain HPQ peptide. Signals from avidin, however, are still present.
FIG. 15C is a SPR-MS spectrum resulting from the subtraction of flow cell 3 from flow cell 2. The peptide signal is not only more prominent (inset), but the background signals (avidin) have been cancelled out.

FIG. 14 shows the sensorgrams obtained during incubation of the SA5 sensor chip with the E. coli lysate system. Of particular interest are flow cells 2 and 3, representing the P1-laced lysate, and the lysate, respectively. It is readily observed that there is no significant difference in the final IA signal response of the two flow cells, although only one (flow cell 2) was exposed to the target analyte (P1). FIGS. 15A through 15C show a baseline subtraction process in which mass spectra from flow cell 3 (lysate background) were subtracted from spectra obtained from flow cell 2 (containing P1). FIG. 15A shows a spectrum obtained from within the confines of flow cell 2. Ion signals are observed due to the retention of P1 (see inset) as well as avidin monomer (m/z~13,000 Da). FIG. 15B shows a mass spectrum obtained within the confines of flow cell 3. Little ion signal in the m/z region of P1 are observed, however, avidin signal is readily observed. Subtraction of the spectrum shown in FIG. 15B from that shown in FIG. 15A yields FIG. 15C. Avidin signals are observed to readily cancel out, yielding a single dominant ion signal signal due to the sodiated P1 ion (m/z calculated=2,229.4 Da; m/z observed= 2,229.1 Da). A second, minor component is observed at m/z~4,500, due most probably to dimerization of P1.

Demonstrated in this example is the use of SPR-MS to unambiguously determine the presence of a specific peptide present in a complex biological mixture. SPR-MS spectra were taken from "active" and "blank" flow cells from which IA analysis yielded little information other than the presence of equal masses of retained material. The spectra were then subtracted from each other to yield a composite mass spectrum which showed the presence of the target analyte.

EXAMPLE 6

Multiplex System (Protein)

Figure 16A:
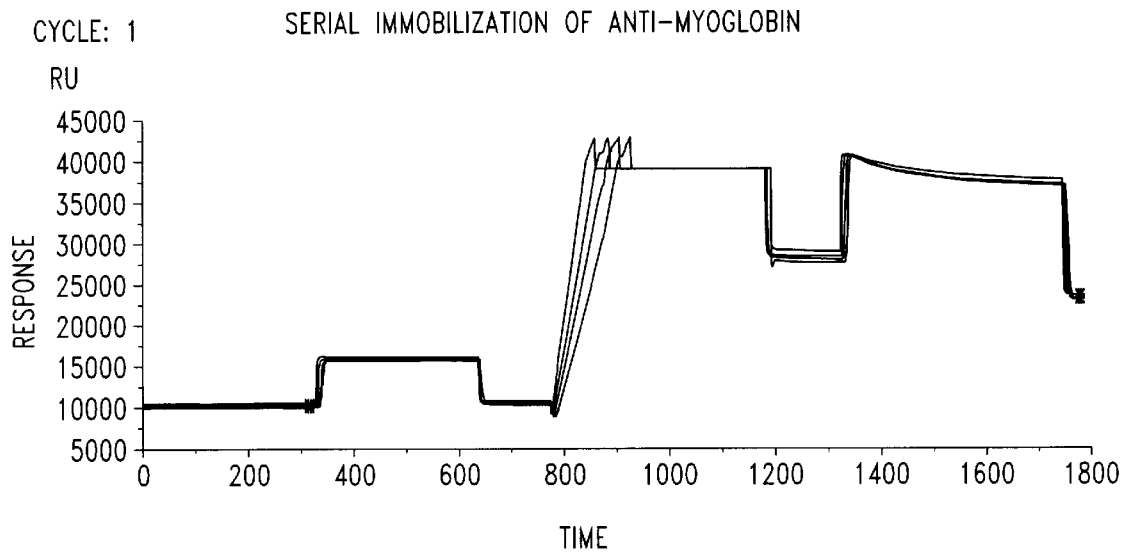
FIG. 16A is a sensorgram of CM5/polyclonal anti-human myoglobin IgG immobilization. All flow cells, except flow cell 4, are derivatized to levels of $\Delta RU=12,000$.
Figure 16B:
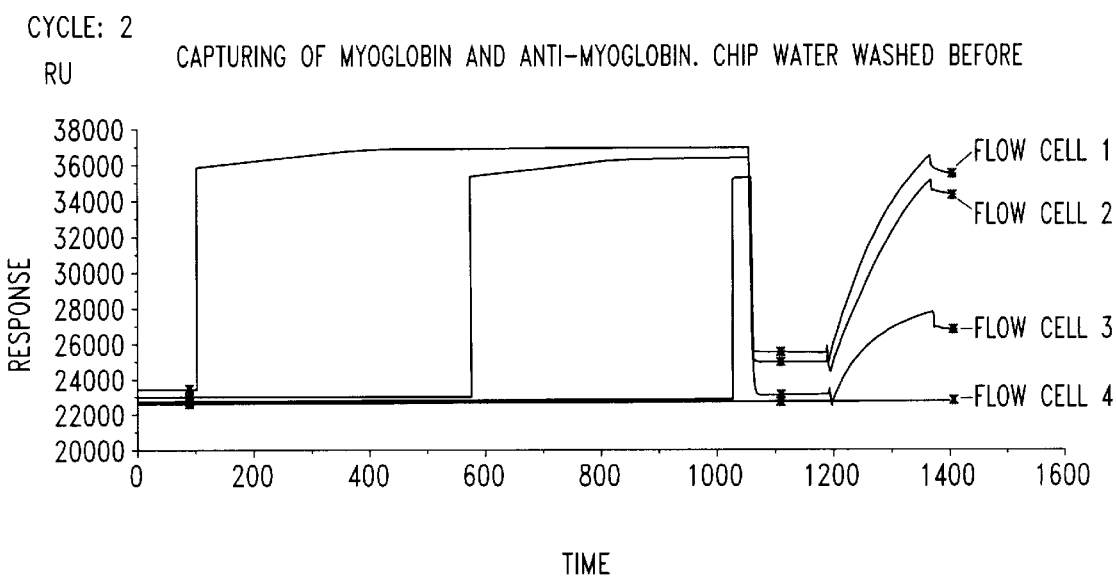
FIG. 16B is a sensorgram of CM5/polyclonal anti-human myoglobin IgG/myoglobin/monoclonal anti-human IgG myoglobin system wherein the derivatized flow cells of FIG. 16A are exposed to human myoglobin for various times in order to retain varying amounts of myoglobin (flow cell 1 and 2 ~100 fmole, flow cell 3~10 fmole). Flow cell 4 serves as a blank. Next the flow cells are exposed to monoclonal anti-human myoglobin IgG, with the sensorgram indicating retention of near-stoichiometric (1:1) amounts of antibody.

Stabilizing agents were washed from a CM5 sensor chip by rinsing the entire surface of the chip with 5 successive 0.2 mL aliquots of distilled water. The chip was then immediately introduced into the Biosensor instrument. All four flow cells of a CM5 sensor chips were derivatized with polyclonal anti-human myoglobin IgG using the same protocols described in Example 3, while monitored using SPR. Surfaces were activated to levels of ~12,000 RU (12 ng/mm$^2$) (FIG. 16A). Individual flow cells were then exposed to human myoglobin (400 ng/mL, in the presence of 20 mg/mL human serum albumin) for various times (0–15 min) resulting with the flow cells retaining between 0 and 100 fmol of myoglobin (FIG. 16B). Subsequent exposure of the flow cells to monoclonal anti-human myoglobin IgG indicated the retention of near-stoichiometric (1:1) amounts the antibody (FIG. 63B)).

Figure 17:
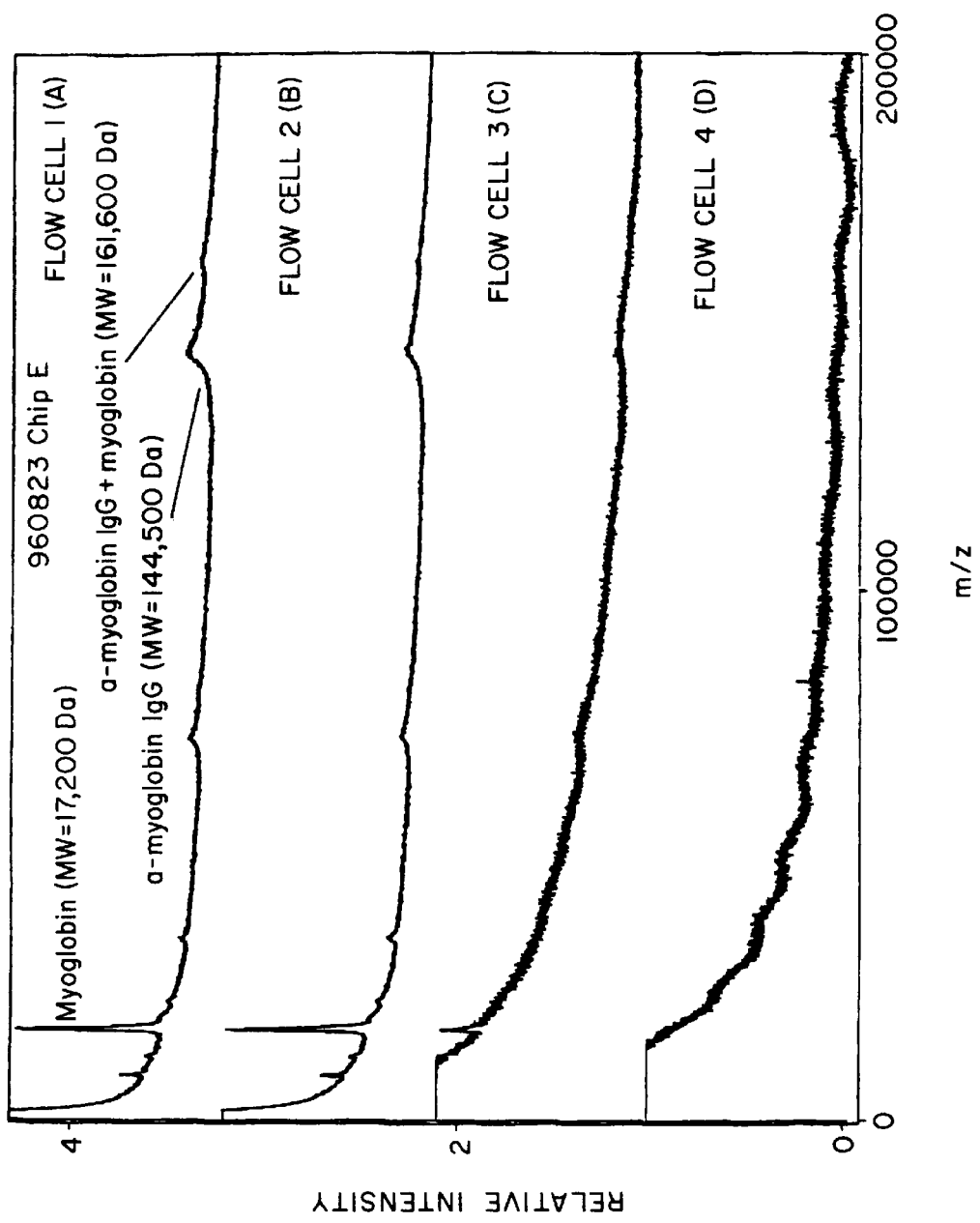
FIG. 17A is a SPR-MS spectrum of the CM5/polyclonal anti-human myoglobin IgG/myoglobin/monoclonal anti-human myoglobin IgG system retained in flow cell 1 of FIG. 17B. Strong signals are observed for myoglobin (m/z=17, 200 Da), anti-myoglobin IgG (m/z=144,500 Da) and the antibody/antigen complex (m/z=161,600 Da).
FIG. 17B is a SPR-MS spectrum of the CM5/polyclonal anti-human myoglobin IgG/myoglobin/ monoclonal anti-human myoglobin IgG system retained in flow cell 2 of FIG. 16B. Again, strong signals are observed for myoglobin, anti-myoglobin IgG and the antibody/antigen complex.
FIG. 17C is a SPR-MS spectrum of the CM5/polyclonal anti-human myoglobin IgG/myoglobin/monoclonal anti-human myoglobin IgG system retained in flow cell 3 of FIG. 16B. Signals are still observed for the myoglobin and anti-myoglobin IgG even at a factor of 10 less analyte retained.
FIG. 17D is a SPR-MS spectrum from flow cell 4, which is the underivatized system that has been exposed to myoglobin and anti-myoglobin IgG. Signals from the myoglobin and anti-myoglobin IgG are not observed.

MALDI mass spectrometry was performed as described in Example 3, except using a MALDI matrix of sinapinic acid (prepared in 1:2, acetonitrile: 1.5% TFA, (SA)). FIGS. 17A, 17B, 17C and 17D show the SPR-MS spectra resulting from the targeting of flow cells 1, 2, 3, and 4, respectively. Strong signals are observed for myoglobin (m/z=17,200 Da), the anti-myoglobin IgG (m/z=144,500 Da) and the antibody/antigen complex (m/z=161,600 Da), when present at the 100 fmole level (FIGS. 17A and 17B). Signals are still observed for the myoglobin and anti-myoglobin IgG when a flow cell containing a factor of ten less analyte was targeted, albeit, with less intense signal (FIG. 17C). Targeting a blank flow cell yielded no signal for either of the species, or the polyclonal antibody used in the original surface derivatization (FIG. 17D).

Demonstrated in this example is the use of SPR-MS to analyze sequential molecular recognition events for the net outcome of stoichiometric relation and observance of second-order biospecific events. Polyclonal anti-human myoglobin IgG was first covalently immobilized to a sensor surface to be used to specifically address myoglobin (as retained from solution). The secondary (monoclonal) antibody was then introduced for binding to the non-covalently retained myoglobin. IA analysis yielded quantitative information on the secondary antibody/myoglobin interaction suggesting an approximately 30% depletion in accessibility to epitope (~100 fmole myoglobin retained, ~70 fmole secondary antibody). This depletion is likely due to shielding of the epitope region by the primary antibody. Mass spectrometry simultaneously confirmed the presence of both binding partners. Of equal importance, mass spectrometry indicated the absence (down to the limit of detection, ~1 fmole) of non-specifically retained material, critical in determining stoichiometric relationships with IA. Finally, observance of the myoglobin/anti-myoglobin IgG complex (FIG. 17A), in the absence of observing IgG signals in the blank spectrum (FIG. 17D), readily differentiates between binding partners of nominally the same molecular weight. Both the primary and secondary antibodies have roughly the same molecular weight (MW~145,000 Da), however, as no signal is observed in the blank, IgG signal is derived from the secondary antibody. The secondary antibody (monoclonal) is therefore indicated as a binding partner in the complex.

EXAMPLE 7

Multiplex System (DNA)

Figure 18A:
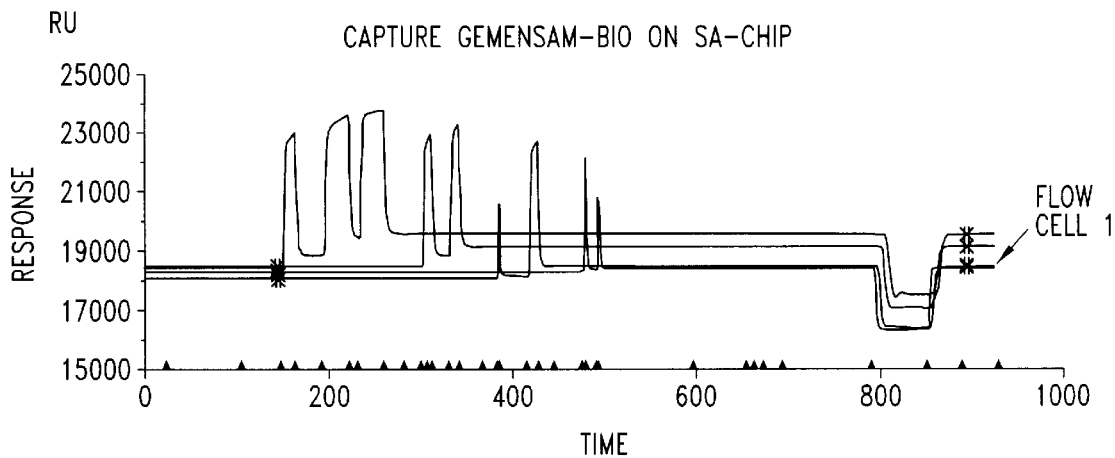
FIG. 18A is a sensorgram illustrating a SA5/streptavidin/ biotinyl-DNA primer immobilization within all four flow cells, with resulting b-DNA primer concentrations ranging from 25 fmole to 250 fmole (flow cell 1 retaining 25 fmole).
Figure 18B:
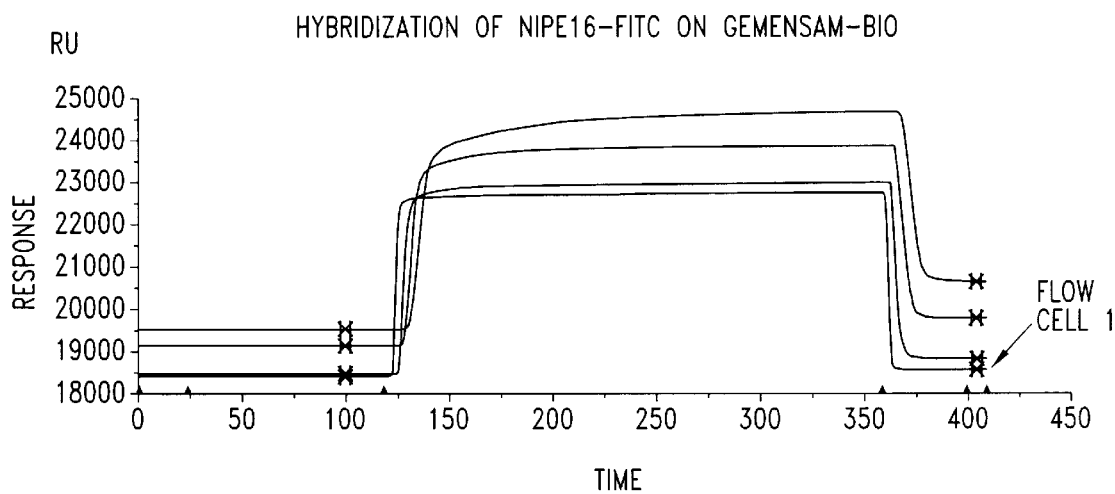
FIG. 18B is a sensorgram illustrating the SA5/streptavidin/ biotinyl-DNA primer/complement DNA system. Flow cells derivatized with b-DNA primer are incubated with a fluorescence-labeled complement of the primer (f-DNA) with a 1:1 retention of the f-DNA observed.
Figure 19:
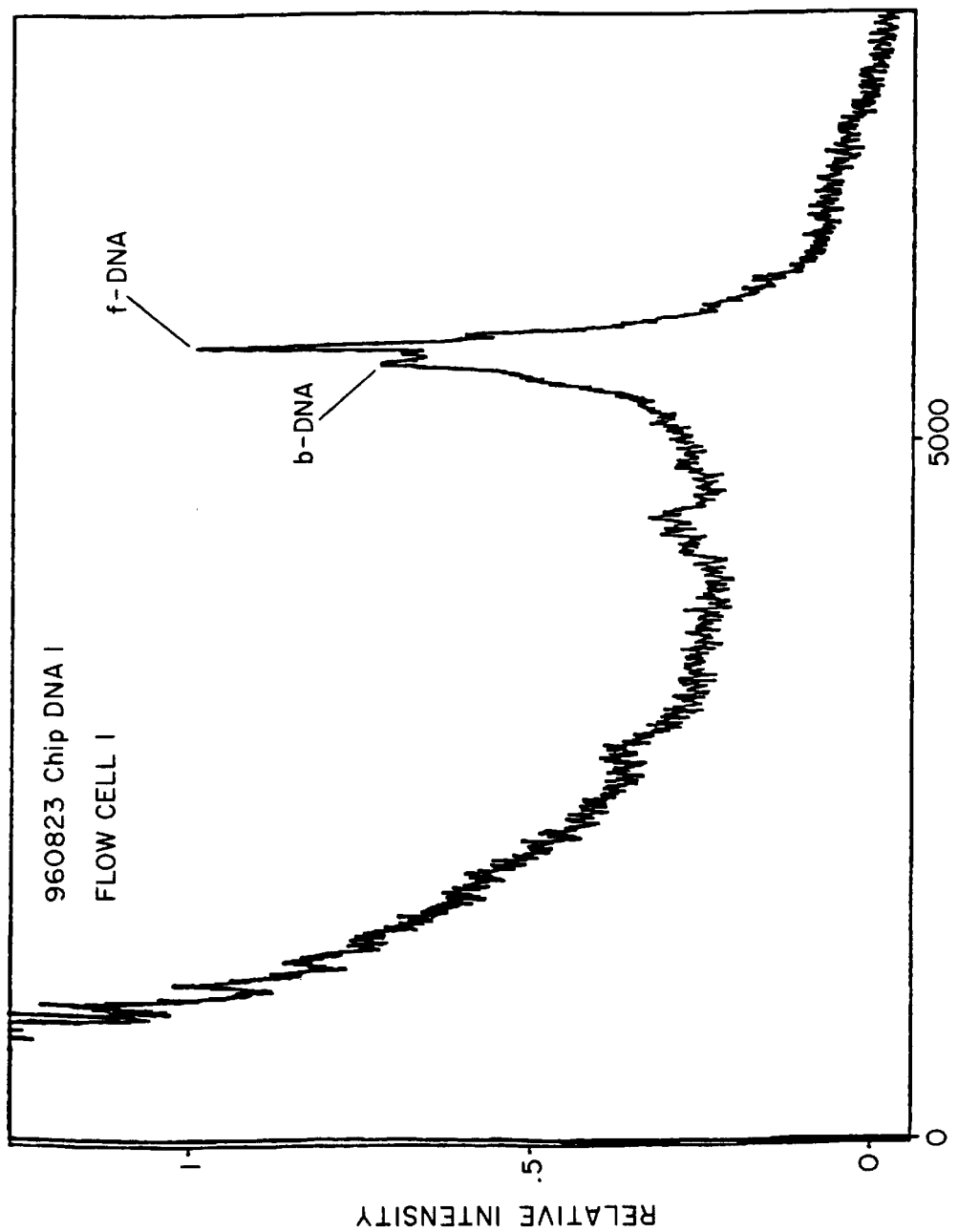
FIG. 19 is a SPR-MS spectrum of the SA5/streptavidin/ biotinyl-DNA primer/complement DNA system retained in flow cell 1 of FIG. 18B (25 fmole of b-DNA and f-DNA). Signals from both b-DNA and f-DNA are observed.

SPR-MS analyses were performed on biotinylated DNA primer: b-3'-TGTTGCGAGATGTCGTC-5'; MW=5,598 Da (b-DNA) using streptavidin (SA5) chips. Individual flow cells were addressed with various amounts of the b-DNA to yield final surface concentrations between $\Delta RU=130$ to 1150 (FIG. 18A). These responses translate to flow cells retaining between 25 to 250 fmole of the b-DNA. The flow cells were then exposed to the fluoroscene-labeled complement of the b-DNA: 5'-ACAACGCTCTACAGCAG-3'-f; MW=5,677 Da ( f-DNA) while under continuous SPR monitoring. Sensorgrams indicated a 1:1 retention of the f-DNA (FIG. 18B). MALDI mass spectrometry was performed as previously described (see Examples 1–6), except using a MALDI matrix of 3-hydroxypicolinic acid (1:2, acetonitrile: 1.5% TFA, 1 mM ammonium acetate (3-HPA)). FIG. 19 shows SPR-MS spectrum resulting from the targeting of flow cell 1 (25 fmole of both b-DNA and f-DNA). Signals due to both b-DNA and f-DNA are observed in the mass spectra with resolution and accuracy adequate to identify each.

This example demonstrates yet another use of SPR-MS to view sequential molecular recognition events. Biotinylated DNA primer is first retrieved from solution, using streptavidin, and then used for selective retrieval of the fluorescence-labeled complement. Sensorgram data indicates a 1:1 stoichiometric relationship between the biotinylated and fluorescence-labeled DNA strands. However, the relative intensity of the two ion signals is not equal, indicating differences in the desorption/ionization, or stability, of the two different DNA strands. Regardless, ion signals capable of readily distinguishing each of the species are apparent in the SPR-MS spectrum.

EXAMPLE 8

Fiber Optic-Based SPR-MS

Figure 20A:
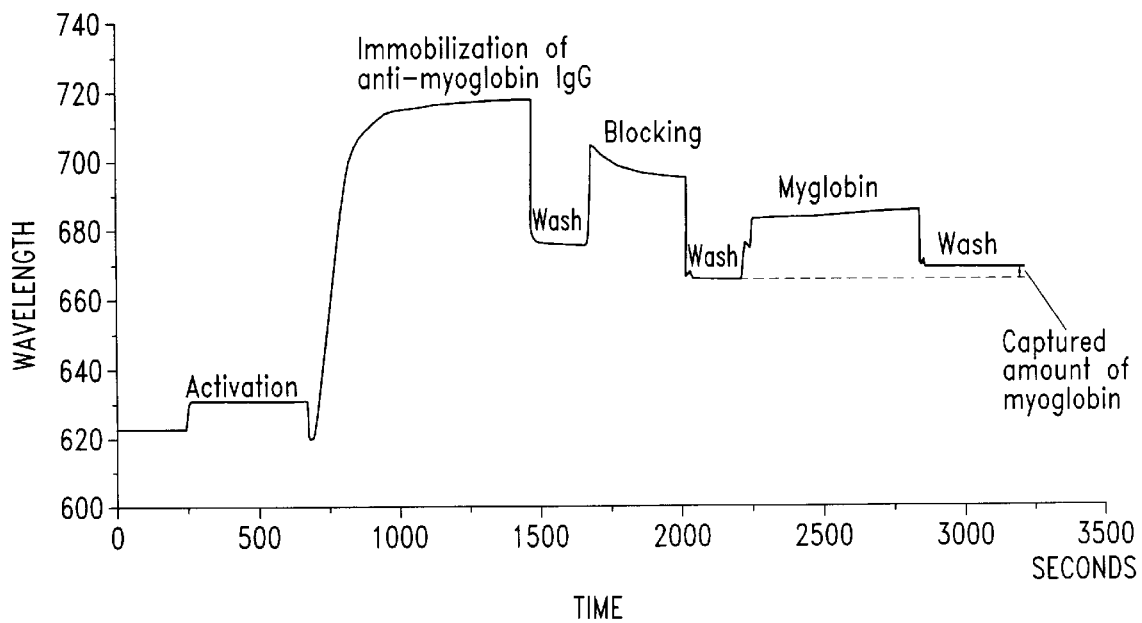
FIG. 20A is a sensorgram and FIG. 20B a SPR-MS spectrum of human myoglobin retained on a polyclonal anti-human myoglobin IgG-derivatized fiber optic SPR probe. Horse heart cytochrome c was added with the sinapinic acid matrix as an internal mass calibrant. Human myoglobin signal is observed an m/z=17,200 Da (asterisks represent non-targeted species retained during the process).
Figure 21A:
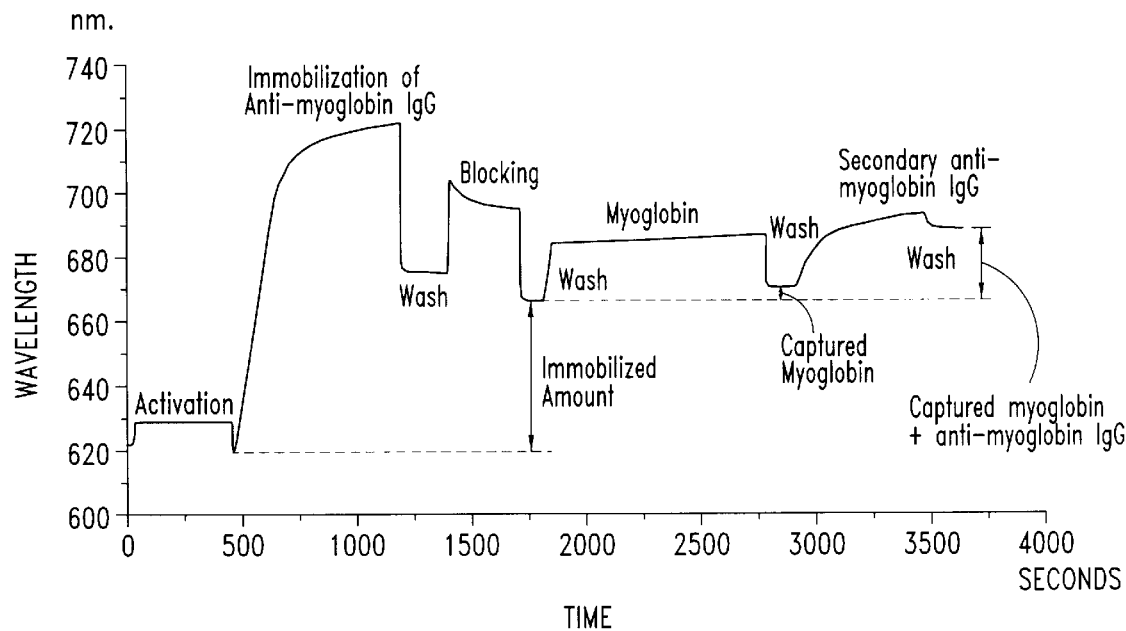
FIG. 21A is a sensorgram and FIG. 21B SPR-MS spectra retained during the incubation of a polyclonal anti-human myoglobin IgG-derivatized fiber optic SPR probe with human myoglobin and subsequently with monoclonal anti-human myoglobin IgG. Signals are observed consistent with the selective retention of human myoglobin and the monoclonal IgG. Signal consistent with the intact antigen/antibody complex is also observed.

SPR-MS analyses were performed on the human myoglobin/anti-human myoglobin IgG system using two fiber optic sensor probes. The interactive surface of the fiber optic sensor probes were as disclosed above in Examples 3 and 6, with the exception that the probes were sequentially dipped in vials containing the various reagents/reactants. Sensorgrams for the fiber optic probes are set forth in FIG. 20A for a polyclonal anti-human myoglobin IgG-derivatized probe, and in FIG. 21A for a polyclonal anti-human myoglobin IgG-derivatized probe with human myoglobin and, subsequently, with monoclonal anti-human myoglobin IgG. It should be noted that instead of RU, the y-axis is reported in terms of wavelength (nanometer) since, in this embodiment, wavelength was scanned instead of incident angle.

Figure 20B:
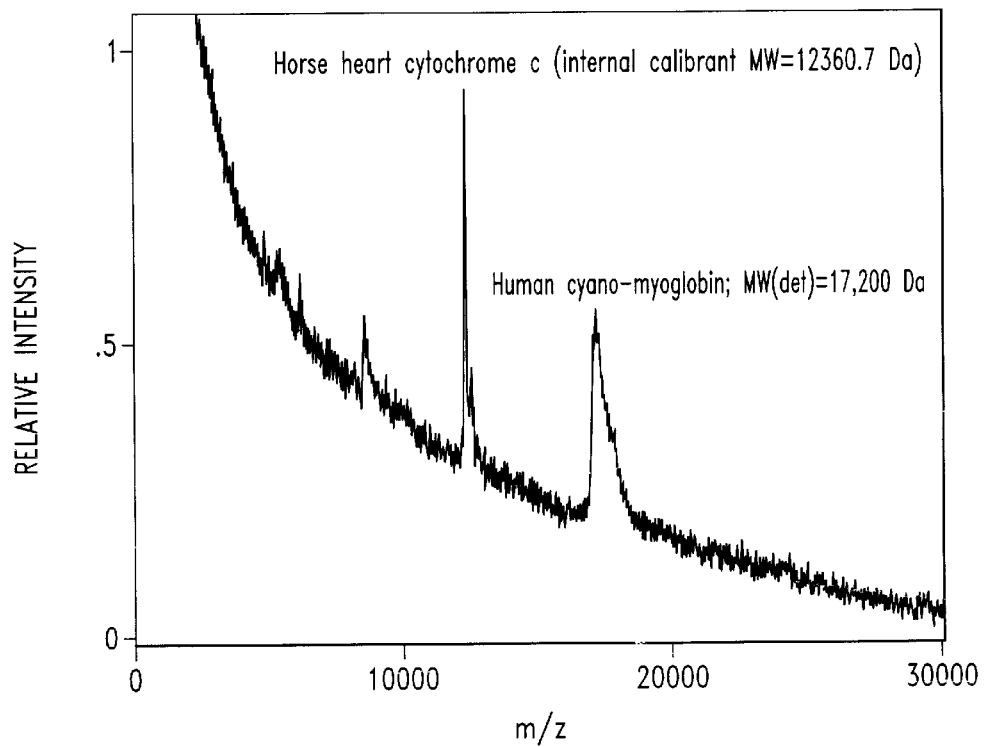
Figure 21B:
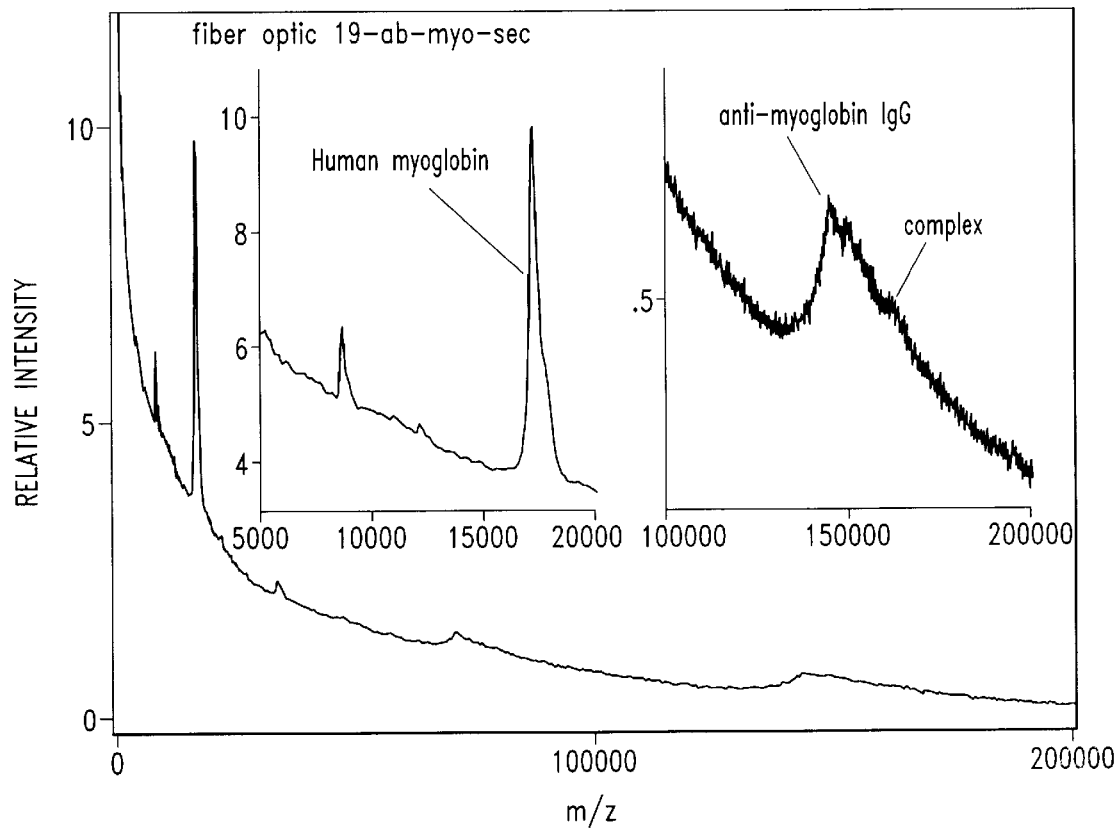

The probes were then exposed to the MALDI matrix sinapinic acid (see Example 6) by rapid insertion of the probe into a vial containing the matrix. The matrix was allowed to air dry before insertion of the fiber optic SPR probe into the mass spectrometer. MALDI mass spectrometry then followed, targeting the fiber optic. FIG. 20B shows the MALDI mass spectrum of human myoglobin retained on the polyclonal anti-human myoglobin IgG-derivatized fiber optic SPR probe. Horse heart cytochrome c (MW=12,360.7 Da) was added with the matrix (as described in Example 2) as an internal mass calibrant. Cyano-stabilized human myoglobin ion signal is observed at m/z=17,200 Da. Other signals are observed in the mass spectrum (marked by *), and are consistent with the non-targeted signals observed in Example 3. FIG. 21B shows a MALDI mass spectrum obtained from polyclonal anti-human myoglobin IgG-derivatized fiber optic SPR probe exposed first to human myoglobin and subsequently to monoclonal anti-human myoglobin IgG (this is the same system as described in Example 6). Ion signals are readily observed for myoglobin (m/z~17,200 Da), the secondary antibody (m/z~144,500 Da) and the antigen/antibody complex (m/z ~161,200 Da).

Demonstrated in this example is the ability to utilize a fiber optic sensor probe in the SPR-MS investigation of sequential biomolecular recognition event.

From the foregoing it will be appreciated that, although specific embodiments of the invention have been described herein for purposes of illustration, various modifications may be made without deviating from the spirit and scope of the invention. Accordingly, the invention is not limited except as by the appended claims.

We claim:

1. A method for performing surface plasmon resonance-mass spectrometry on a sample, comprising:

capturing an analyte present within the sample by an interactive surface layer of an interaction analysis sensor;

analyzing the analyte by surface plasmon resonance which monitors a consequential change of a reflected first light beam while the analyte is captured by the interactive surface layer of the interaction analysis sensor; and mass analyzing the captured analyte by desorbing/ionizing the analyte from the interactive surface layer of the interaction analysis sensor with a second light beam while under vacuum within a mass spectrometer.

2. The method of claim 1 wherein the interaction analysis sensor is a sensor chip.

3. The method of claim 1 wherein the interaction analysis sensor is a fiber optic sensor.

4. A method for analyzing and identifying an analyte within a sample, comprising:

capturing the analyte by contacting the analyte with an interactive surface layer affixed to a conductive material capable of supporting surface plasmon resonance, wherein the conductive material has a front surface affixed to the interactive surface layer and a back surface affixed to a transparent layer;

directing a first light beam through the transparent layer at varying angles of incidence or wavelengths such that the first light beam is reflected off the back surface of the conductive material and excites surface plasmons at the interface between the conductive layer and the interactive surface laser;

detecting the angle of incidence or the wavelength at which the intensity of the reflected first light beam has a minimum due to surface plasmon resonance to determine the angular or wavelength change caused by the analyte captured by the interactive surface layer; and measuring the mass spectrum of the analyte by desorbing/ionizing the analyte from the interactive surface layer with a second light beam while under vacuum within a mass spectrometer.

5. The method of claim 4 wherein the interactive surface layer affixed to the conductive material and the transparent layer is in the form of a chip.

6. The method of claim 4 wherein the interactive surface layer affixed to the conductive material and the transparent layer is in the form of a fiber optic.

7. The method of claims 1 or 4 wherein the interactive surface layer is a hydrogel.

8. The method of claim 7 wherein the hydrogel is a hydrogel of a polysaccharide.

9. The method of claim 8 wherein the polysaccharide is a carboxymethylated detran.

10. The method of claim 4 wherein the conductive material is a metal.

11. The method of claim 10 wherein the metal is gold.

12. The method of claim 4 wherein the transparent layer is a glass.

13. The method of claim 4 wherein the first light beam is polarized light.

14. The method of claims 1 or 4 wherein the second light beam is laser light.

15. The method of claim 4 wherein the second light beam is laser light directed at the interactive layer such that it passes through the interactive layer before striking the front surface of the conductive material.

16. The method of claim 4 wherein the second light beam is laser light directed at the interactive layer such that it strikes the back surface of the conductive material and passes through the conductive material and into the interactive layer.

17. The method of claims 1 or 4 wherein, prior to desorbing/ionizing the analyte, it is contacted with a laser desorption/ionization matrix.

* * * * *